(12) United States Patent
Prescott

(10) Patent No.: US 6,454,791 B1
(45) Date of Patent: *Sep. 24, 2002

(54) LASER THERAPY FOR FOOT CONDITIONS

(76) Inventor: Marvin A. Prescott, 833 Moraga Dr., Suite 15, Los Angeles, CA (US) 90049

( * ) Notice: Subject to any disclaimer, the term of this patent is extended or adjusted under 35 U.S.C. 154(b) by 0 days.

This patent is subject to a terminal disclaimer.

(21) Appl. No.: 09/611,361

(22) Filed: Jul. 6, 2000

Related U.S. Application Data

(63) Continuation of application No. 09/025,874, filed on Feb. 18, 1998, now Pat. No. 6,156,028, and a continuation-in-part of application No. 08/829,247, filed on Mar. 31, 1997, now Pat. No. 5,989,245, and a continuation-in-part of application No. 08/703,488, filed on Aug. 26, 1996, now Pat. No. 5,814,039, and a continuation-in-part of application No. 08/215,263, filed on Mar. 21, 1994, now Pat. No. 5,616,140.

(51) Int. Cl.[7] .............................................. A61N 5/067
(52) U.S. Cl. ......................................... 607/89; 607/88
(58) Field of Search ...................... 606/1–9; 607/88–89

(56) References Cited

U.S. PATENT DOCUMENTS

| | | | |
|---|---|---|---|
| 3,327,712 A | 6/1967 | Kaufman et al. | 128/398 |
| 4,517,974 A | 5/1985 | Tanner | 128/303 |
| 4,538,609 A | 9/1985 | Takenaka et al. | 128/303.1 |
| 4,576,160 A | 3/1986 | Tanaka | 128/303.1 |
| 4,660,925 A | 4/1987 | McCaughan, Jr. | 350/96.15 |
| 4,669,467 A | 6/1987 | Willett et al. | 128/303.1 |
| 4,676,246 A | 6/1987 | Korenga | 607/153 |
| 4,718,417 A | 1/1988 | Kittrell et al. | 606/7 |
| 4,744,624 A | 5/1988 | Burston | 350/96.2 |
| 4,848,339 A | 7/1989 | Rink et al. | 128/303.1 |
| 4,860,172 A | 8/1989 | Schlager et al. | 362/32 |
| 4,878,891 A | 11/1989 | Judy et al. | 604/5 |
| 4,881,547 A | 11/1989 | Danforth | 606/194 |
| 4,915,108 A | 4/1990 | Sun | 607/96 |
| 4,930,504 A | 6/1990 | Diamantopoulos et al. | 607/88 |
| 4,982,742 A | 1/1991 | Claude | 128/798 |
| 5,000,752 A | 3/1991 | Hoskin et al. | 606/9 |
| 5,029,581 A | 7/1991 | Kaga et al. | 128/398 |
| 5,029,970 A | 7/1991 | Hengst et al. | 350/96.2 |
| 5,034,235 A | 7/1991 | Dunn et al. | 426/238 |
| 5,040,548 A | 8/1991 | Yock | 128/898 |
| 5,059,191 A | 10/1991 | Beyer et al. | 606/2 |
| 5,061,273 A | 10/1991 | Yock | 606/194 |
| 5,142,598 A | 8/1992 | Tabone | 385/78 |
| 5,161,526 A | 11/1992 | Hellwing et al. | 128/395 |
| 5,163,935 A | 11/1992 | Black et al. | 606/17 |
| 5,178,617 A | 1/1993 | Kuizenga et al. | 606/17 |
| 5,188,632 A | 2/1993 | Goldenberg | 606/7 |
| 5,201,317 A | 4/1993 | Kanazawa et al. | 600/342 |
| 5,221,279 A | 6/1993 | Cook et al. | 606/15 |
| 5,234,407 A | 8/1993 | Teirstein et al. | 604/528 |
| 5,248,311 A | 9/1993 | Black et al. | 606/15 |
| 5,259,380 A | 11/1993 | Mendes et al. | 607/115 |
| 5,261,904 A | 11/1993 | Baker | 606/17 |

(List continued on next page.)

OTHER PUBLICATIONS

Abstracts of the First Cong. of the World Assoc. of Laser Therapy, *Laser Therapy*, vol. 8(1), Apr., 1996, 5 pp.

(List continued on next page.)

*Primary Examiner*—Linda C. M. Dvorak
*Assistant Examiner*—Henry M. Johnson
(74) *Attorney, Agent, or Firm*—David A. Farah; Sheldon & Mak PC

(57) ABSTRACT

A laser insole having one or many vertical cavity surface emitting lasers embedded therein may be worn by a patient and applied to an area of the foot. The device supplies the patient with a preprogrammed laser therapy regimen. A physician programs the device in a patient's shoe. The device is small enough to allow the patient's normal activities. The laser therapy regimen promotes healing of a wound on the foot. Alternatively, the device may be adapted as a flexible device applied to the skin, or implanted into the body, or provided in a catheter that is inserted into a body region.

14 Claims, 12 Drawing Sheets

U.S. PATENT DOCUMENTS

| | | | |
|---|---|---|---|
| 5,267,993 A | 12/1993 | Grace et al. ................. | 606/11 |
| 5,272,716 A * | 12/1993 | Soltz et al. ................ | 372/109 |
| 5,292,414 A | 3/1994 | Sessler et al. ............. | 204/157 |
| 5,300,097 A | 4/1994 | Lerner et al. ................ | 607/93 |
| 5,330,517 A | 7/1994 | Mordon et al. .............. | 607/89 |
| 5,334,171 A | 8/1994 | Kaldany ...................... | 604/20 |
| 5,336,184 A | 8/1994 | Teirstein ............... | 604/103.04 |
| 5,344,419 A | 9/1994 | Spears ......................... | 606/15 |
| 5,358,503 A * | 10/1994 | Bertwell et al. ............. | 606/27 |
| 5,370,615 A | 12/1994 | Johnson ................ | 604/102.02 |
| 5,380,316 A | 1/1995 | Aita et al. ..................... | 606/7 |
| 5,395,361 A | 3/1995 | Fox et al. ..................... | 606/15 |
| 5,405,369 A | 4/1995 | Selman et al. ................ | 607/89 |
| 5,437,659 A | 8/1995 | Leckrone ....................... | 606/7 |
| 5,445,608 A * | 8/1995 | Chen et al. ................... | 604/20 |
| 5,470,352 A | 11/1995 | Rappaport ................. | 607/101 |
| 5,479,543 A | 12/1995 | Black ......................... | 385/31 |
| 5,484,433 A | 1/1996 | Taylor et al. ................ | 607/17 |
| 5,500,009 A * | 3/1996 | Mendes et al. .............. | 607/88 |
| 5,505,726 A | 4/1996 | Meserol ......................... | 606/9 |
| 5,514,126 A | 5/1996 | Prescott ....................... | 606/10 |
| 5,531,738 A | 7/1996 | Hessel et al. ................. | 606/2 |
| 5,540,659 A | 7/1996 | Teirstein .................... | 604/104 |
| 5,558,672 A | 9/1996 | Edwards et al. ............. | 606/41 |
| 5,571,152 A | 11/1996 | Chen et al. ................... | 607/92 |
| 5,616,140 A | 4/1997 | Prescott ....................... | 606/10 |
| 5,620,438 A | 4/1997 | Amplatz et al. ............. | 606/10 |
| 5,620,439 A | 4/1997 | Abela et al. .................. | 606/11 |
| 5,624,433 A | 4/1997 | Radisch, Jr. ................... | 606/7 |
| 5,658,262 A | 8/1997 | Castaneda et al. .......... | 604/264 |
| 5,662,712 A | 9/1997 | Pathak et al. .............. | 600/195 |
| 5,702,439 A | 12/1997 | Keith et al. ................... | 604/96 |
| 5,728,090 A | 3/1998 | Martin et al. .................. | 606/3 |
| 5,741,246 A | 4/1998 | Prescott ......................... | 606/7 |
| 5,766,234 A | 6/1998 | Chen et al. ................... | 607/92 |
| 5,800,478 A | 9/1998 | Chen et al. ................... | 607/88 |
| 5,814,039 A | 9/1998 | Prescott ......................... | 606/7 |

OTHER PUBLICATIONS

Abstracts from the 68th Scientific Sessions, p. I–33, Circulation (Suppl.) 92:1995, 0151–0154.

American Society for Laser Medicine and Surgery Abstracts, p. 9, containing Abstract Nos. 36, 39 and 43.

Bibikova et al., "Attenuation of the Process of Skeletal Muscle Regeneration by Low Level Energy Laser Irradiation," *Journal of Low Level Laser Therapy and Photobioactivation*, Abstracts: Walt 1996, vol. 8, No. 1, (Apr. 1996).

Enwemeka et al., "Biomechanical Effects of Three Different Periods of GaAs Laser Photostimulation on Tenotomized Tendons," *Journal of Low Level Therapy and Photobioactivation*, (Jun. 1, 1994).

Enwemeka, Chukuka S., "Laser Biostimulation of Healing Wounds: Specific Effects and Mechanisms of Action," *The Journal of Orthopaedic and Sports Physical Therapy*, 9(10):333–338 (1988).

Gal et al., "Percutaneous Delivery of Low–Level Laser Energy Reverses Histamine–Induced Spasm in Atherrosclerotic Yucatan Microswine," *Circulation*, 86:756–768 (1992) (only p. 756 enclosed).

Kipshidze, "Our Experience in the Use of a Low Intensity HeNe Laser in the Treatment of Acute Myocardial Infarction," *Journal of Low Level Laser Therapy and Photobioactivation*, Abstracts: Walt 1996, vol. 8, No. 1, (Apr. 1996).

Kirichuk et al., "Influence of Low Power Laser Radiation on Plateelet Aggregation in Pathological Stress," *Journal of Low Level Laser Therapy and Photobioactivation*, Abstracts: Walt 1996, vol. 8, No. 1 (Apr. 1996).

Kleinman et al., "Low Level Laser Therapy in Patients with Venous Ulcers: Early and Long–term Outcome," *Journal of Low Level Laser Therapy and Photobioactivation* (Jul. 1996).

Petrischey et al., "Laser Irradiation on Blood Platelets," *Journal of Low Level Laser Therapy and Photobioactivation*, Abstracts: Walt 1996, vol. 8. No. 1 (Apr. 1996).

Quickview Report, Piper Jaffray Research, CardioGenesis Corporation, Jun. 20, 1996, pp. 5 and 6.

Samioliova et al., "Photochemotherapy in Clinical and Veterinary Medicine: Therapeutic Effects and Mechanisms," *Journal of Low Level Therapy and Photobioactivation*, Abstracts: Walt 1996, vol. 8, No. 1, Apr. 1996.

Schneider, R.P. Jr., "GaInAsP/AIGaInP–Based Near–IR (780nm) Vertical–Cavity Surface–Emitting Lasers," *Electronic Letters*, 31(7):554–555 (Mar. 30, 1995).

Whittaker, P., "Collagen and ventricular remodeling after acute myocardial infarction: concepts and hypotheses," *Steinkopff Verlag* (1997).

Whittaker, et al., "Role of Collagen in Acute Myocardial Infarct Expansion," *Circulation*, 84(5):2123–2134 (Nov. 1991).

Yu et al., "The Effect of Laser Irradiation on the Release of bFGF from 3T3 Fibroblasts," *Photochemistry and Photobiology*, 59(2):167–170 (1994) (Only p. 756 enclosed).

* cited by examiner

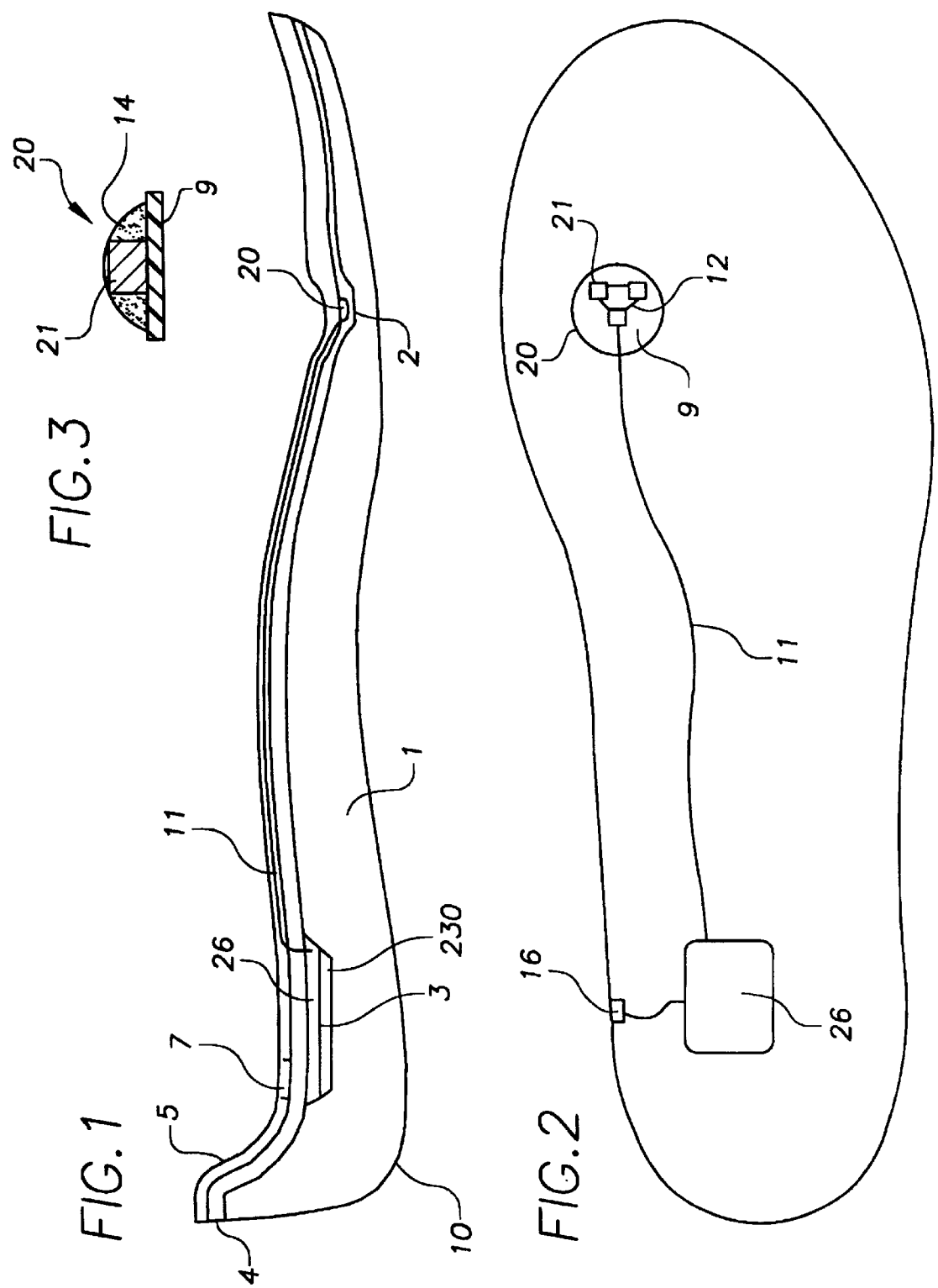

LASER THERAPY FOR FOOT CONDITIONS

CROSS-REFERENCE TO RELATED APPLICATIONS

This application is a continuation of U.S. patent application Ser. No. 09/025,874, filed Feb. 18, 1998 entitled "Method and Apparatus for Therapeutic Laser Treatment of Wounds; now U.S. Pat. No. 6,156,028" and a continuation-in-part of U.S. patent application Ser. No. 08/829,247, filed Mar. 31, 1997, entitled "Method and Apparatus for Therapeutic Laser Treatment," now U.S. Pat. No. 5,989,245, issued Nov. 23, 1999; and a continuation-in-part of Ser. No. 08/703,488, filed Aug. 26, 1996 entitled "Laser Catheter," now U.S. Pat. No. 5,814,039, issued Sep. 29, 1998; and a continuation-in-part of U.S. patent application Ser. No. 08/215,263 filed Mar. 21, 1994 entitled "Method and Apparatus for Therapeutic Laser Treatment," now U.S. Pat. No. 5,616,140 issued Apr. 1, 1997, each of which is incorporated by reference herein in their entirety.

BACKGROUND

1. Field of the Invention

The present invention is directed to a method and apparatus for applying low level laser therapy in the treatment of certain medical conditions. Specifically, the present invention is directed to a method and apparatus for low level laser therapy using vertical cavity surface emitting lasers (VCSELs) to enhance healing of difficult-to-heal wounds by promoting increased circulation and increased tensile strength of the healed wound. More particularly, the present invention is directed to a method for healing diabetic ulcers, venous stasis ulcers, and pressure ulcers and to prevent their recurrence. Additionally, the present invention is directed to a method and apparatus for balancing blood chemistry, stimulating the immune system, and improving endocrine function in diabetic patients.

2. Description of Related Art

Diabetes is a large and growing problem in the United States and worldwide, costing an estimated $45 billion dollars to the U.S. health care system. Patients afflicted with diabetes often have elevated glucose and lipid levels due to inconsistent use of insulin, which can result in a damaged circulatory system and high cholesterol levels. Often, these conditions are accompanied by deteriorating sensation in the nerves of the foot. As a result, diabetics experience a high number of non-healing foot ulcers.

It is estimated that each year up to three million leg ulcers occur in patients in the U.S., including venous stasis ulcers, diabetic ulcers, ischemic leg ulcers, and pressure ulcers. The national cost of chronic wounds is estimated at $6 billion. Diabetic ulcers often progress to infections, osteomyelitis and gangrene, subsequently resulting in toe amputations, leg amputations, and death. In 1995,approximately 70,000 such amputations were performed at a cost of $23,000 per toe and $40,000 per limb. Many of these patients progress to multiple toe amputations and contralateral limb amputations. In addition, the patients are also at a greatly increased risk of heart disease and kidney failure from arteriosclerosis which attacks the entire circulatory system.

The conventional methods of treatment for non-healing diabetic ulcers include wound dressings of various types, antibiotics, wound healing growth factors, skin grafting including tissue engineered grafts, and hyperbaric oxygen. In the case of ischemic ulcers, surgical revascularization procedures via autografts and allografts and surgical laser revascularization have been applied with short term success, but with disappointing long term success due to reclogging of the grafts. In the treatment of patients with venous stasis ulcers and severe venous disease, antibiotics and thrombolytic anticoagulant and anti-aggregation drugs are often indicated. The failure to heal and the frequent recurrence of these ulcers points to the lack of success of these conventional methods. In addition, the number of pressure ulcers (i.e., bed sores) continues to grow with the aging of the population, and these can be particularly difficult to heal in bedridden or inactive patients. Accordingly, the medical community has a critical need for a low cost, portable, non-invasive method of treating diabetic, venous, ischemic and pressure ulcers to reduce mortality and morbidity and reduce the excessive costs to the health care system.

The application of laser beam energy in the treatment of medical conditions is known. Studies have shown that low power laser beam energy (i.e., 1–500 mw) in varying wavelengths (i.e., 400–1,300 nm ) delivering 0.5–10 $J/cm^2$ is effective in the treatment of various medical conditions. Studies have shown that low power laser therapy (LLLT) stimulates fibroblasts and other cells important in the wound healing process to release a number of growth factors in greater amounts than without laser photostimulation, thus enhancing and accelerating the wound healing process. Increased proliferation of fibroblasts and keratinocytes has been reported in a number of studies as well as the release of cytokines from Langerhans cells and the release of growth factors from macrophages.

For example, Wei Yu reported in PHOTOCHEMISTRY AND PHOTOBIOLOGY 1994, that low energy laser irradiation increased the release of basic fibroblast growth factor (BFGF). Basic fibroblast growth factor is a potent mitogen and chemoattractant for fibroblasts and endothelial cells and induces a predominantly angiogenic response in the healing wound. These growth factors can stimulate growth of new blood vessels in the healing wound, stimulate increased proliferation of fibroblasts, and increased collagen deposition, and result in increased tensile strength of the healing scar. Also, Enwemeka reported an increased tensile strength after laser therapy in healing rabbit tendons in LASER THERAPY JOURNAL 1994. A significant clinical demonstration of the increased tensile strength of scars of healed venous stasis ulcers was reported recently by Kleinman et al. in LASER THERAPY JOURNAL 1996.

The effects of low power laser therapy on blood vessels and circulation have also been reported. Bibikova and Uoron reported in LASER THERAPY JOURNAL 1996 that healing after muscle injury was accelerated by low power laser irradiation and demonstrated significant new formation of blood vessels (i.e., angiogenesis) at the injury site. They postulated that an increased oxygen supply from increased circulation contributes to the accelerated healing effect. Gal reported in CIRCULATION 1992 a photorelaxation effect in atherosclerotic microswine via transcutaneous laser irradiation and postulated a direct effect on smooth muscle cells in the blood vessel walls, thus increasing the circulation of arterioles and opening reserve capillaries.

Transcutaneous application of low level laser therapy has been reported to alter blood biochemistry, hemostasis, erythrocyte and leukocyte blood count, and platelet aggregation. Salansky et al. reported in a human clinical trial in THE AMERICAN SOCIETY OF LASER MEDICINE AND SURGERY a significant elevation of leukocytes and erythrocytes after transcutaneous application of low level laser energy. Samoilova et al. reported in THE LASER THERAPY JOURNAL 1996 that transcutaneously irradiated blood increased the oxygen carrying capacity of blood, decreased red blood cell viscosity, improved microcirculation, normalized hemostasis and activated the immune system. The main effectors of the above events appear to be photomodified lymphocytes, monocytes, and platelets.

Several studies have reported the effect of LLLT on healing infected wounds. Palmgren reported accelerated wound healing of infected abdominal wounds in a human clinical study in AMERICAN SOCIETY OF LASER MEDICINE AND SURGERY 1991. Koshelev reported in LASER THERAPY 1996 that laser therapy as an adjunct to conventional therapy for infected-necrotic diabetic ulcers along with $CO_2$, laser surgery reduced high amputations from 44% to 25% and decreased mortality from 9% to 1%.

Clinical studies of the transcutaneous effect of LLLT in treating diabetes have been published. Lyaifer reported in LASER THERAPY 1996 that transcutaneous laser blood irradiation was as effective as intravascular blood irradiation in treating diabetic angiopathy. Onuchin reported in LASER THERAPY 1996 that a combination of transcutaneous treatment of the pancreas and intravenous blood irradiation reduced insulin requirements by 45% and normalized the immune system in 80% of a laser-treated group of insulin dependent diabetics (IDDM) for up to six months. Kleinman reported in LASER THERAPY 1996 on a clinical trial using transcutaneous LLLT on forty-four diabetic patients with chronic foot ulcers who failed all conservative treatments and were scheduled for limb amputation. Seventy five percent had complete or partial healing of the ulcer.

In the treatment of foot and leg ulcers where there is poor circulation (i.e., ischemic limb), surgical vascular grafting often becomes necessary. Vascular grafting may result in a short term improvement. Over the long term, however, a major cause of relapse has been the proliferation of smooth muscle cells in the newly anastomosed graft with the smooth muscle cells arising both from the graft and the anastomosed vessel. In CIRCULATION 1992, Kipshidze reported the potential of LLLT to reduce smooth muscle proliferation and accelerate endothelial regeneration in atherosclerotic arteries treated with balloon angioplasty. In addition, Onuchin reported in LASER THERAPY 1996 that LLLT reduces the high cholesterol blood levels in IDDM patients, balances blood biochemistry, stimulates better endocrine function and stimulates the immune system.

Conventional low power laser devices generally comprise a hand held probe with a single laser beam source, or a large stationary table console with attached probe(s) powered by a conventional fixed power supply. A common laser beam source is a laser diode which is commercially available in varying power and wavelength combinations. Large probes which contain multiple laser diodes affixed to a stand are also known. Such large, multibeam devices are typically very expensive and require extensive involvement of medical personnel when treating a patient. A large probe containing multiple beam sources is typically affixed to a stand which has to be focused and controlled by a doctor or ancillary medical personnel.

In addition to the cost of the device and the treatment therewith, such a device requires a patient to travel to the location of the laser treatment device in order to obtain the laser therapy. Studies have shown that such treatment typically must be provided on a regular basis (e.g., every few hours or daily for up to thirty minutes at each application) in order to be effective and to produce optimum results. This requires numerous patient visits to the treatment facility and extended treatment times at each visit to produce the desired effect. As it is common for problems to arise which necessitate the patient missing a treatment visit to the treatment facility, or for patients to be inconsistent in the times at which they are available for appointments, the efficacy of the treatment regimen may be lowered or the length of the treatment and the number of patient visits increased.

Accordingly, a critical need exists for a method and apparatus for low power laser therapy of difficult-to-heal ulcers and wounds that is economical, convenient and more efficient than was previously possible. Therefore, a primary object of the present invention is to provide an effective system for healing difficult-to-heal wounds and ulcers and prevent recurrence of these ulcers. Another object of the invention is to provide a compact device that is readily available in an emergency situation and that can be worn by a patient without interfering with the patient's normal activities. Yet another object of the invention is provide a low cost method for long term therapy as a preventive measure to diabetic ulcers and wounds.

SUMMARY OF THE INVENTION

The present invention overcomes the problems associated with prior art laser therapy devices by providing a method and apparatus for low power laser therapy of difficult-to-heal ulcers, particularly diabetic ulcers, venous stasis ulcers, and pressure ulcers. More specifically, the present invention solves the problems associated with the need for constant physician attention and inconsistent treatment delivery. The present invention also provides for a relatively low cost, efficient, and portable method for treating difficult-to-heal ulcers and as an adjunct to traditional methods for treating diabetic hormonal imbalance and imbalances of the blood and immune systems that occur in that disease.

To achieve the above and other objectives, a preferred embodiment of the present invention utilizes vertical cavity surface emitting lasers (VCSELs) to deliver laser beam energy in a treatment regimen focused on the region of the ulcer and over any involved organ or blood vessel. The VCSELs allows for the application of such treatments in a manner which does not require constant physician or ancillary medical personnel attention once the device is activated, programmed, and applied to the appropriate site.

More particularly, the present invention provides a laser therapeutic device for applying laser treatment to the area of an ulcer in a systematic, preprogrammed manner to obtain optimum results while decreasing the cost associated with such treatment. The device includes a flexible circuit which is integrated onto a shoe insole for treating foot ulcers. The insole is placed inside the patient's shoes or socks. The flexible circuit is coupled to a power supply which is disposed on the bandage or on the insole. A plurality of VCSELs or VCSEL arrays are disposed in the flexible circuit and are operatively connected to the power supply. A controller is also operatively connected to the power supply and the VCSELs or VCSEL arrays, and causes the VCSELs to fire for a predetermined period of time at specified intervals. A treatment regimen is stored by the controller. The VCSELs and controller are sandwiched between a clear hydrophobic membrane housing and the insole so as to present a smooth surface to the bottom of the foot and so as to direct the laser beams to the treatment area of interest on the foot. A clear wound dressing, such as a polyurethane hydrocellular material, may be applied to the wound or ulcer to provide a sterile environment and the laser insole placed against this material.

In operation, the physician may program a specific regimen in the device and allow the patient to wear the device inside the shoes or socks for an appropriate time period for healing, thus requiring less frequent visits for monitoring. As a result of the portability, design and efficiency of application, laser therapy delivered by this method is more efficient as well as more cost effective than prior devices. Another advantage of this invention is that the patient is able to wear the device preventatively on a long term basis at home, according to need and a physician's prescription to prevent recurrence of the ulcer.

In a second embodiment of the present invention, a bandage device using a number of VCSELs or VCSEL arrays may be positioned over the ulcer or adjacent to the ulcer. In this embodiment the VCSELs, programmable controller and power supply are sandwiched between a clear, biocompatible polymer. The bandage is attached to the patient using a medical adhesive affixed to the laser emitting side of the device. To provide a more sterile environment and protect the wound, a wound dressing such as a clear polyurethane hydrocellular dressing or a hydrogel is placed over the wound and then a disposable clear microporous hydrophobic membrane sheet (MHM) may be attached to the skin. The bandage device adheres to this film. In operation, a physician may program a specific treatment regimen in the device and allow the patient to wear the device attached to the body for an appropriate time period for healing, thus requiring less frequent visits for monitoring. In addition, the patient may be directed to wear the device on a long term basis for preventive maintenance once the wound or ulcer is healed.

In a third embodiment of the present invention, a bandage having two side sections is provided. Each side section preferably has a half-moon shape and surrounds an area of treatment on the patient's body. A plurality of VCSELs or VCSEL arrays are disposed within the bandage and are coupled to a controller/power supply, as described above. The VCSELs systematically provide low-level laser therapy to a wide area proximate the wound area. The ends of each side bandage section may be connected to each other using a flexible polymer material.

In a fourth embodiment of the present invention, the laser beam energy is delivered to the area of interest (e.g., wound, vasculature, organs, body cavities, etc.) through the use of optical fibers coupled to the VCSELS. The optical fibers may be temporarily implanted in the area of treatment interest using minimally invasive surgery. As with the previously discussed embodiments, a programmable source of laser beam energy coupled to the fibers permits the fibers to transmit the laser beam along their length to the region of treatment interest.

In a fifth embodiment of the present invention, the VCSELs are disposed on a flexible circuit in the shape of a disc or strip, which provides an implanted source of low level laser energy directly to an area within the patient's body. The VCSELs may be arranged circularly or in parallel on the flexible circuit. The flexible circuit is operatively connected to a controller/power supply which is attached to the patients body near the region of treatment interest. The flexible circuit is implanted by minimally invasive surgery into the area of treatment interest adjacent to that area and positioned to irradiate the designated area. Thus, low-level laser therapy may be effectively applied to the treatment area to promote increased circulation and function of the kidneys and pancreas or any other designated organ or body area.

In a sixth embodiment of the present invention there is provided device having foldable arms carrying circuits on which VCSELs are mounted. The foldable arms open like an umbrella after insertion into a patient. The VCSELs are disposed at the respective ends of the foldable arms.

In a seventh embodiment of the present invention, a catheter is provided with VCSELs or VCSEL arrays. The catheter is inserted into the vasculature to deliver laser energy treatment to an artery after balloon angioplasty, vascular graft surgery or other artery opening procedure. This embodiment can also be used as a flexible laser therapy device to provide low level laser therapy to a deep wound, body orifice or canal, or to provide low level laser therapy during open surgical procedures. The catheter may also be provided with an optically clear, inflatable balloon for performing balloon angioplasty having VCSELs placed distal to the balloon toward the tip of the catheter for unobstructed delivery of the laser energy during a balloon procedure. Alternatively, the VCSELs would be placed inside an optically clear balloon to provide laser therapy during inflation of the balloon and after.

In an eighth embodiment of the present invention, a needle catheter has VCSELs disposed on a side surface thereof. The needle is inserted into an area of interest of the patient to deliver laser energy to an affected area.

A more complete understanding of the method and apparatus for therapeutic laser treatment of diabetic ulcers and wounds will be afforded to those skilled in the art, as well as a realization of additional advantages and objects thereof, by a consideration of the following detailed description of the preferred embodiment. Reference will be made to the appended sheets of drawings which will first be described briefly.

BRIEF DESCRIPTION OF THE DRAWINGS

FIG. 1 is a cross-sectional side view of a first embodiment of a laser therapeutic apparatus in accordance with the present invention;

FIG. 2 is a top plan view of the first embodiment of FIG. 1;

FIG. 3 is an enlarged sectional side view of a laser circuit used in the apparatus of FIG. 1;

DETAILED DESCRIPTION OF THE PREFERRED EMBODIMENT

Figure 4:
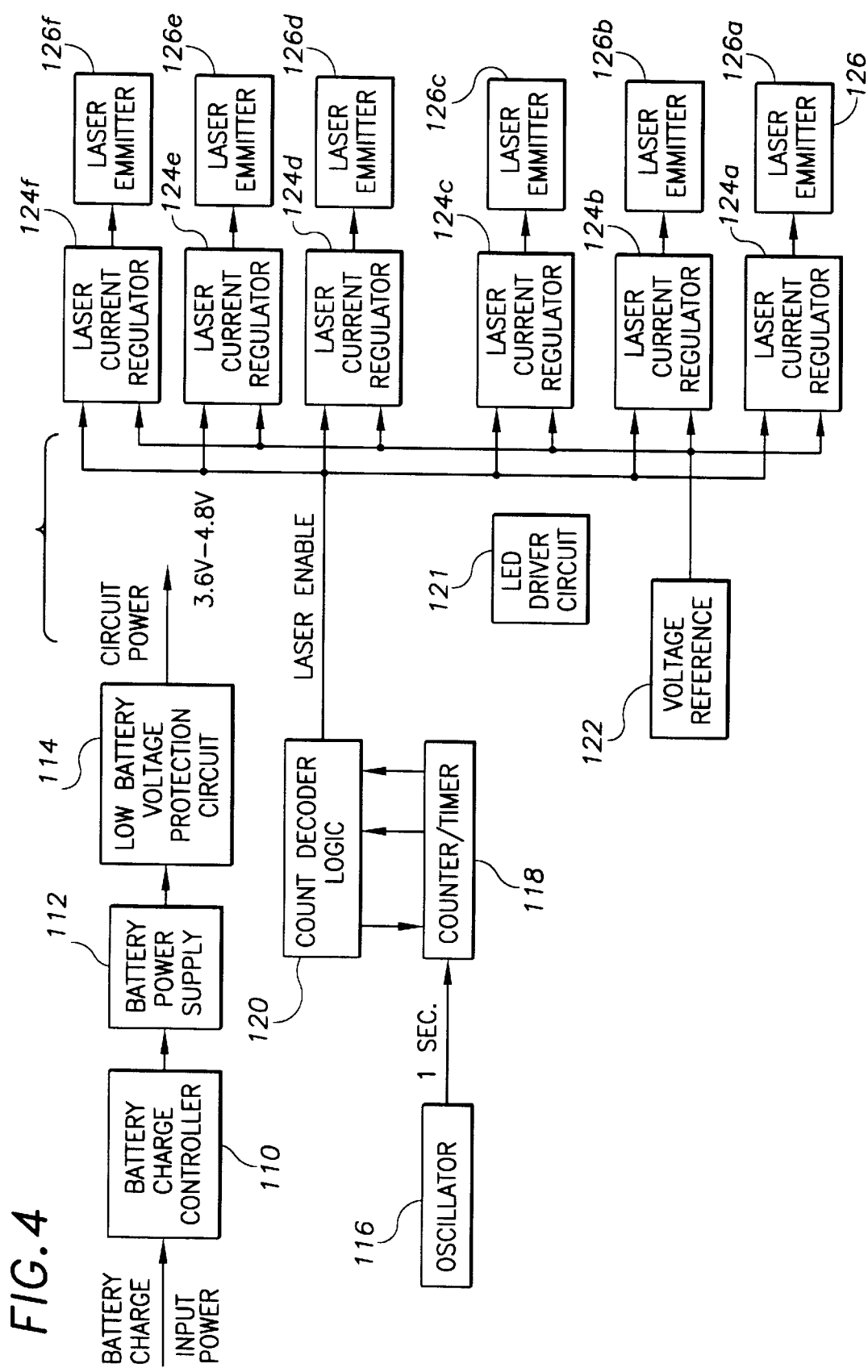
FIG. 4. is a block diagram showing a preferred embodiment of a power supply and control circuit for the laser therapeutic device of FIG. 1.

The present invention satisfies the need for a method and apparatus for low power laser therapy of difficult-to-heal ulcers and wounds that is economical, convenient and more efficient than was previously possible. It should be understood that the following discussion of the preferred embodiment of the invention is not to be considered in a limiting sense. Rather, it is to be understood that numerous modifications, additions, and/or substitutions can be made to the preferred embodiment without departing from the spirit and scope of the present invention.

Referring first to FIGS. 1–3, a first embodiment of the present invention is illustrated.

As shown in FIG. 1, a laser therapeutic device 10 includes an orthotic insole base 1. The insole base 1 may be comprised of polymer, composite fiber or other is appropriate orthotic construction materials. A first relief area 2 is provided in the insole base 1 in the region of an ulcer to be treated. A second relief area 3 is placed in the heel area of the insole base 1 in which the controller/power supply 26 is disposed. A cushioning layer 4, such as comprised of poron material of approximately 1/10 inch thickness, is placed over the insole base 1 for cushioning and enclosing the controller/power supply 26.

A laser treatment circuit 20 is disposed in the first relief area 2 of the insole 1 above the cushioning layer 4. The circuit 20 includes an array of lasers or individual lasers 21 electrically connected in series, such as using conductive printed ink interconnects 12. The plurality of lasers 21 are encapsulated in an optically clear epoxy material 14 to maintain the relative position of the lasers and present a low profile for the circuit 20. The circuit 20 is further disposed on a substrate 9, which may be comprised of a flexible polyester material. The circuit 20 is operatively connected to the controller/power supply 26 via an electrical interconnect 12.

The lasers 21 of the circuit 20 are activated by an activating switch 7. The activating switch 7 is a pressure switch which is operatively connected to the programmable controller/power supply 26. Switch 7 is activated by the patients' foot pressure or by a medical attendant. The circuit 20 laser array and activating switch 7 are sandwiched between a hydrophobic biocompatible layer 5, such as a clear polymer layer of 0.5 millimeter thickness, and the cushioning material 4. This way, the surface of the laser insole facing the foot surface follows the contour of the cushioning material layer, with the circuit 20 disposed in the relief area 2 to prevent any pressure on the ulcer. A recharge receptacle or recharge contact 16 is disposed on the side of the heel area on base 1, and is electrically connected to the controller/power supply 26.

The lasers 21 are preferably vertical-cavity surface emitters (VCSELs) having a nominal output power of 1.5 mw and a wavelength on the order of 400–1300 nm, with the preferred power output at least 5–10 mw per VCSEL and the preferred wavelength being between 760 to 850 nanometers. VCSELs comprise semiconductor lasers which emit a beam normal to the surface of the semiconductor substrate. The semiconductor includes aluminum arsenide (AlAs) or gallium arsenide (GaAs) or a combination thereof. Each VCSEL has a self-contained, high reflectivity mirror structure forming a cavity to produce the beam. Additional lenses may be used to focus or defocus the beam. A typical VCSEL may be on the order of 300 micrometers long, 200 micrometers in height and have an operational power threshold below 12 ma and reach maximum output of 4–5 mw at around 18 ma, thus consuming very little power compared to conventional laser diodes and enabling numerous VCSELs to be powered from a single battery source. For purposes of this invention, it should be clear that the terms "laser(s)" and "VCSEL (s)" are used interchangeably. Various forms of medical treatment using lasers and VCSELs are disclosed in U.S. Pat. No. 5,616,140, issued Apr. 1, 1997, for METHOD AND APPARATUS FOR THERAPEUTIC LASER TREATMENT, the subject matter of which is incorporated herein by reference.

In the present invention, a VCSEL chip with submount for surface mounting (chip mounts) requires only about 150 microns in height including the submount. The submount comprises a heat sinking material such as silicon, ceramic copper, or aluminum nitride, and contacts (i.e., anode and cathode) are positioned so that the VCSEL can be surface mounted on a circuit, such as the circuit 20 of FIG. 1. The VCSEL would be mounted on the submount and wire-bonded to the submount or alternatively flip-chip bonded. In the flip-chip version, both contacts would be on the bottom of the unit, thus increasing the manufacturing reliability. The VCSEL chip is encased in an optically clear epoxy encapsulant, resulting in a low-profile laser device. A single VCSEL 20 may be contained in a chip or an array of VCSELS may be used, each chip having two to four VCSELS. A number of different wavelengths could be combined with each chip having its own specific wavelength, those wavelengths ranging from 400–1300 nm. The VCSEL devices are then distributed an the circuit material in accordance with the design of the device and are interconnected using electrical connectors or by printed conductive ink interconnects. A polymer battery may be surface mounted on the reverse side of the circuit carrying the controller/power supply 26 or attached to the controller/power supply and covered with a 0.5 millimeter clear, biocompatible polymer which is scaled to the cushioning layer of the orthotic insole.

The programmable controller/power supply 26 provides power and timing control for operation of the lasers. The programmable controller/power supply 26 may be initiated by a single-pole, double-throw switch, or by pressure switch 7. The timing control performed by the controller/power supply 26 includes initiating the operation of the lasers for a predetermined time period in accordance with a prescribed laser treatment regimen. A control device performing such a function is known in the art and may comprise a programmable controller having a 24-hour timing function which initiates operation of the laser for a predetermined period of time over the course of a 24-hour period. Preferably, the therapeutic device of the present invention is programmed to deliver two minutes of laser therapy at four-hour intervals for five to six days at which time it would be recharged or a new battery installed. To prevent the device from being accidentally deprogramed during the critical healing period, the switch 7 with an "on-only" switch that cannot be turned off by the patient.

As intended in the preferred embodiment, when the patient inserts the laser orthotic device 10 inside the shoe and stands erect, the pressure switch would automatically initiate a preprogrammed treatment regimen. After removal of the shoe, the pressure switch 7 would open in the absence of pressure, and the patient would be required to manually trip the pressure switch and apply the orthotic to the foot surface, preferably by placing the device 10 inside a sock. Alternatively, the device 10 may include a standard on/off switch that does not initiate programming of the device, but rather initiates laser firing immediately.

A preferred embodiment of a controller/power supply circuit 26 is shown in FIG. 4. A battery charge controller 110, which may be connected to an external power source, supplies a battery power supply 112 with a charge when the charge controller 110 is connected to the external source. When an optimum charge level is reached, the charge controller ceases supplying the battery 112 with the charge. Preferably, the battery 112 is capable of maintaining a charge sufficient for one week of laser therapy based on a treatment being provided for two minutes every four hours or a duty cycle of less than 5%; however, a different duty cycle may be selected based on the application. A low battery voltage protection circuit 114 regulates the power supplied by the battery 112 and provides a voltage output between 3.6 and 4.8 volts. The protection circuit 114 ceases the supply of power if the voltage drops below the threshold level of 3.6 volts to avoid damage to the circuit components. The power supplied by the protection circuit 114 is used to power the circuit components as well as the lasers. An oscillator 116 is provided which supplies pulses at one second intervals to counter/timer circuit 118. The counter/timer circuit 118 counts the pulses while a count decode logic circuit 120 monitors the count.

The count decode logic circuit 120 is a multipurpose logic circuit which may comprise, for example, a PAL (programmable array logic) or a PLA (programmable logic array) that may be programmed to detect certain counts, e.g., 14,400 which would correspond to four hours of time and 120 which would correspond to two minutes of time. The count decode logic circuit 120 would be capable of maintaining the stored timing program (and, therefore, the prescribed regimen) without power being applied thereto. The count decode logic circuit 120 may also comprise a discrete logic, circuit formed of standard logic components. While such a circuit would be more cost effective from a low-volume manufacturing perspective, the preferred count decode logic 120 comprises a programmable logic circuit to afford maximum flexibility in operation of the laser therapeutic device of the present invention.

Upon detection of the programmed count, the decode logic circuit 120 outputs a laser enable pulse which enables laser current regulator circuits 124*a–f* which regulate the power to each laser emitter 126*a–f* (corresponding to the lasers 21 of FIGS. 1–3). The regulator circuits 124*a–f*, which are known in the art and which compare the current with a known voltage reference in order to maintain a constant current output, receive a voltage reference input from a voltage reference circuit 122. The voltage reference circuit 122 may comprise an active bandgap zener diode which supplies a constant voltage output (e.g., on the order of 1.2 to 1.5 volts) regardless of the voltage of the battery 112. At the same time, the count decode logic 120 provides a RESET pulse to the counter/timer circuit 118 to reset the count, and the counter/timer circuit 118 continues counting the pulses from the oscillator 116.

The laser enable pulse remains active for the programmed length of treatment, e.g., two minutes, or 120 counts of the counter/timer circuit 118. While enabled, the current regulators 124*a–f* use the input from the voltage reference circuit 122 to provide a predetermined amount of current to produce a beam having a desired power level, such as 4.2 mw. The beams are produced by the laser emitters 126*a–f*. The logic circuit 120 continues to monitor the count in the counter 118 and detects when the count reaches a programmed amount corresponding to the prescribed treatment length (e.g., 120) and then terminates the laser enable pulse. At the same time, the logic circuit 120 provides a RESET pulse to reset the count in the counter/timer circuit 118, and the cycle begins again.

To preserve battery power, the count decode logic circuit 120 may be programmed to provide a pulse to individual ones of the regulator circuits 124*a–f*. This configuration permits sequential firing of the VCSEL arrays rather than simultaneous firing. Thus, particular areas of the wound or ulcer area may be pinpointed for laser treatment. Alternatively, multiple laser enable pulses may be provided.

In operation, the laser therapeutic device 10 may be used to accelerate and enhance healing of a foot ulcer or wound by promoting angiogenesis, increased circulation, and increased tensile strength of the wound by increasing collagen deposition in the wound. In the case of a bone fracture, device 10 may be used to accelerate the healing of the bone in the foot area. Thus, in operation, the laser therapeutic device 10 would be placed inside the patient's shoe by the physician or ancillary medical personnel or worn inside a sock to deliver a programmed laser biostimulation treatment regimen. An appropriate clear wound dressing would be placed first to minimize attenuation of the laser beam. The lasers 20 would be positioned in the relief area 2 of a custom orthotic insole and focused on the area of the ulcer. In the case of a pressure ulcer on the heal, a strip of lasers 21 would be placed in the heel area of the insole 11 posterior to the controller/power supply 26. Alternatively, the lasers 21 may be distributed over the entire surface of the orthotic insole facing the foot bottom in an off-the-shelf version of insole device 10.

The controller/power supply circuit 26 may be disposed on a single circuit board which may be sufficiently thin (e.g., on the order of less than 1 mm) to be encapsulated by a polymer sheet and be formed integral therewith. Alternatively, the controller/power supply circuit 26 may also be comprised of multiple circuit components which are readily available from electronics suppliers or may be implemented in an application specific integrated circuit (ASIC) to reduce size and complexity thereof.

Referring again to FIG. 2, the partial cross-sectional side view of the laser therapeutic device 10 shown in FIG. 1 reveals a circuit 20 with a plurality of VCSELs 21 disposed thereon and coupled to the controller/power supply 26. In an embodiment of the invention, the circuit 20 may be formed on a non-conductive polyester material in which the electrical interconnects and circuit design are printed with flexible, electrically conductive ink, such as developed by Polyflex Circuits Corporation. Flexible circuits may also be made using ULTEM (a trademark of General Electric Corp) or Kapton (a trademark of Dupont Corp). The VCSELs 21 are sealed by a clear epoxy chip encapsulant 14 shown in FIG. 3 and the circuit 20, controller/power supply circuit 26 and pressure switch 7 are fixed and sealed to the cushioning 4 layer with a biocompatible clear hydrophobic polymer layer of 0.5 mm thickness, which results in a perfectly smooth surface on the top side of the insole facing the foot bottom.

The controller/power supply circuit 26 preferably includes a 6 volt, wafer thin, flexible polymer battery by ECR Ltd., Israel, and a programmable controller. The ECR battery technology comprises hydrogen ion storage electrodes and an extremely high rate solid state electrolyte, is rechargeable and completely environmentally friendly. The technology allows manufacture as conformable films. The ECR battery can also be printed directly on flexible circuit material. Another clear advantage is the one minute quick recharge capability of the ECR battery without damaging the battery which would allow duty cycles greater than 5%. The battery also could be a simple 3–6 volt battery or a rechargeable nickel-metal hydride battery. Preferably, the battery can provide sufficient power for a seven day treatment regimen. Alternatively, a transformer or other appropriate power supply may be used. A power supply would transform household AC voltages to DC voltages for use by the device.

The operation of the therapeutic device 10 is initiated by the switch 7. The switch 7 may have an LED incorporated therein to indicate function or battery status of the device 10. Preferably, the switch 7 is also covered by the biocompatible polymer layer 5, is a pressure switch that activates the preprogrammed treatment regimen but automatically disengages and shuts off the system when no pressure is applied for a predetermined time period, such as 30 minutes. This allows laser therapy to be applied while the patient is wearing the device and saves battery power when the patient is not wearing the device. Alternatively, an on/off switch would activate the device if it is to be worn inside a sock, slipper, or directly affixed to the foot when the patient is sleeping or is non-ambulatory. If an on/off switch version is selected, a time period can be provided between the operation of the switch 7 and the actual initiation of the laser treatment regimen to allow sufficient time for the therapeutic device 10 to be properly positioned on the patient's foot prior to initiation of laser therapy.

In the case of a diabetic ulcer, a clear hydrogel dressing (e.g., Intrasite by Smith & Nephew) is applied and then a clear polyurethane hydrocellular dressing (e.g., OpSite by Smith-Nephew or Omiderm by ITG), is placed over the hydrogel to prevent bacterial contamination of the wound. The polyurethane protective film prevents bacterial contamination of the laser device and allows penetration of the laser beam in the treatment area without attenuation of the beam. Alternatively, only a polyurethane hydrocellular dressing such as OpSite or Omiderm may be placed over the wound. In operation, this dressing prescription would allow once a week change of the dressing and increase the efficiency of healing.

After the patient or medical personnel places the laser insoles in the shoes and the patient puts on the shoes, foot pressure on the pressure switch 7 activates the system and laser therapy begins. In operation, the laser energy from the device 10 irradiates the appropriate treatment area of the foot ulcer. Specifically, the VCSEL arrays 21 are repetitively fired at the appropriate wavelength and power so as to penetrate with patient's foot. Wavelengths within a range of 400 to 1300 manometers may be selected, although the preferred wavelength is 780 manometers.

The controller/power supply 26 is preferably a low-power consumption device which is capable of approximately one week of operation from a single battery charge. Therapeutic devices 10 having a different treatment regimen preprogrammed therein could be provided, with the physician selecting a particular device in accordance with an appropriate regimen depending on the patients' condition. Alternatively, the controller/power supply 26 may be provided with a PCMCIA port which interfaces with a so-called "smart card" or master programming card which can be inserted therein and a treatment regimen may be downloaded to the controller 26 by the treating physician.

After being placed in the patient's shoe or sock, the patient simply wears the laser insole therapeutic device 10 for the prescribed time period. The therapeutic device 10 automatically delivers the prescribed laser therapy as determined by the programmable controller/power supply 26. Thus, the time-consuming, costly, and ill-timed applications of the prior art laser treatment regimens are replaced by an efficient, programmed laser treatment regimen over a prescribed time period. In the treatment of general foot problems not involving ulceration, the laser insole device 10 could be stocked in an off-the-shelf adaptable version to be used for a variety of foot injuries and fractures in a routine or an emergency basis. In this embodiment a number of VCSELs or VCSEL arrays would be distributed over the surface of the device 10.

A clear advantage of the treatment using the laser therapeutic device 10 is the freedom provided to the patient. For example, depending on the nature of the prescribed laser therapy, the patient may only need to wear the device 10 during certain hours of the day (e.g., while sleeping) or full time, without interfering with a normal lifestyle. The device can be easily and rapidly recharged to provide extended treatment times. Additionally, the patient's visits to the physician can be reduced to a minimum and the patient can wear the device on a long term basis to maintain the improvement in circulation and tissue health, thus reducing the potential for further ulceration, infections, and life threatening amputations.

Figure 5:
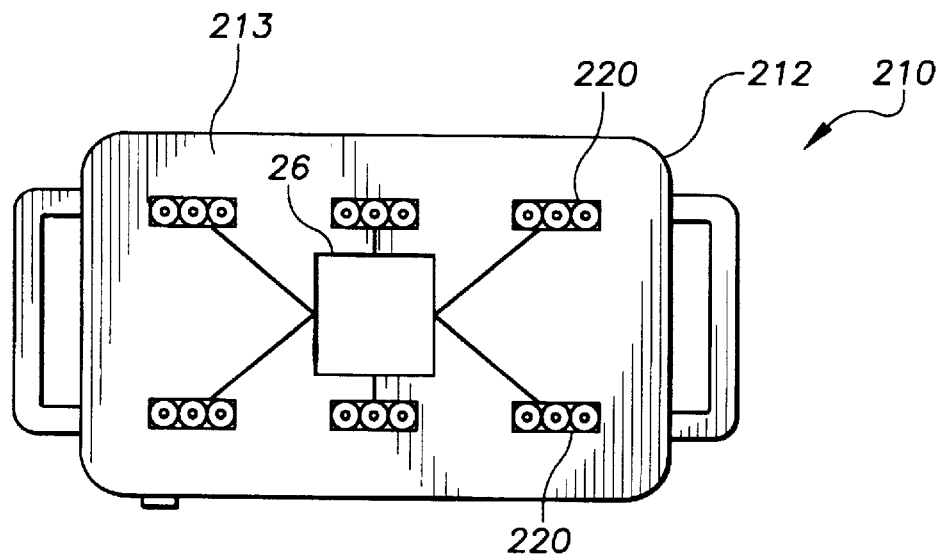
FIG. 5 is a top plan view of a second embodiment of a laser therapeutic device in accordance with the present invention.
Figure 6:
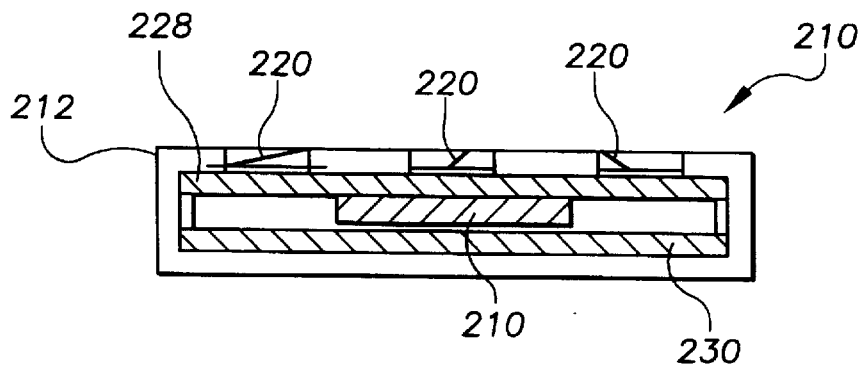
FIG. 6 is a cross-sectional view of the second embodiment of a laser therapeutic device shown in FIG. 5.

FIGS. 5–6 illustrate a second embodiment of the laser therapeutic device. Referring to FIG. 5, a laser therapeutic device 210 in accordance with the second embodiment is in the form of a flexible bandage and includes a clear biocompatible polymer body or housing 212. In addition, an optically clear, breathable sterile polymer sheet may be affixed to the skin of the patient prior to attaching the device 210 to prevent contamination of the device or skin irritation. Preferably, an assortment of VCSEL chips 220 are distributed over an area of the surface 213 of a circuit material 228 (see FIG. 6) and are interconnected, such as by to electrically conductive printed ink interconnects. A controller 226 is mounted on the circuit 228 to control operation of the VCSELs as substantially described above.

Microchip sensors to monitor heart and body functions may be included in the device and information regarding these functions may be relayed to a central nurse's station for monitoring the patient's status. To enable this function, a wireless LAN design-in module could be incorporated with the control circuit 226. This allows high-performance wireless LAN communications to be embedded in a wearable computing device and empowers portable devices by linking them to servers and other resources on a wired network.

A polymer battery 230 may be surface-mounted an the reverse side of the circuit material 228 or alternatively, printed directly on the circuit. The entire device 210 is sealed in a biocompatible polymer which is optically clear on the laser emitting side to allow transmission of the laser beam and can be flesh tone or other color on the exposed side. The biocompatible housing material having a thickness of roughly 0.25–0.50 millimeters results in a flexible sheet or bandage of lasers (including VCSELS, IC's, logic, and battery) having a total thickness of approximately 4 millimeters.

In operation, the laser therapeutic device 210 may be used to enhance healing of an ulcer or wound by promoting increased circulation, increased fibroblast proliferation and collagen deposition, reduced infections through stimulation of the immune system and increased tensile strength of the healed wound. The device 210 is affixed proximate to the wound/ulcer or directly over the wound after placing a clear microporous membrane sheet (MHM) over the wound area to prevent bacterial contamination of the wound and laser device. Alternatively, a clear hydrogel can be placed on the wound. Then a clear polyurethane hydrocellular film as previously described placed over the hydrogel. The laser device 210 would then be affixed to the patient using a medical adhesive. A second such laser device 210 may be placed over a major artery, such as the femoral or popliteal, to increase circulation, balance the biochemistry of the blood system, reduce excess lipid levels, increase tissue oxygen tension, reduce platelet aggregation, and stimulate the immune system. Additionally, the laser therapeutic device 210 could be placed over the pancreas or kidney reflex points or focused directly on the area of the pancreas or kidney to aid the function of both organs. This could be prescribed on an alternating basis such as one day on the pancreas reflex points and the next day on the kidney reflex points and the next day an the pancreas reflex points, and so forth.

In operation, the attending physician may mark the exact location of device 210 on the patient's skin over the pancreas, kidney or selected blood vessel with a waterproof marking pen. The patient will not be permanently marked using such a pen, since the body will naturally eliminate the marks over the course of one to two weeks. In this manner, the sterile, optically-clear biocompatible sheet can be changed each time the device is relocated and ancillary medical personnel or the patient can accurately position the device each time. In the preferred treatment program for foot ulcers, the laser orthotic insole 10 of FIGS. 1–3 would be placed in operation and the laser bandage 210 of FIG. 5–6 placed over a blood vessel such as the femoral or popliteal as described above. Additionally, a second laser bandage 210 may be placed over the pancreas or pancreas reflex points to improve endocrine function. In the case of a venous ulcer, a laser bandage device 210 may also be placed over a vein to enhance venous circulation.

After being located on the patient's body, the patient simply wears the therapeutic device for the prescribed period of time. The therapeutic device automatically delivers the prescribed laser therapy as determined by the programmable controller. In this fashion, the attending physician or other medical personnel places the therapeutic device on the appropriate area of the patient's body adjacent to the area of interest. The time-consuming, costly, and ill-timed applications of the prior art laser treatment devices are replaced by an efficient, programmed laser treatment regimen over the course of a week. On an emergency basis, the attending personnel may be performing other time critical tasks while the laser therapy is being administered automatically. Due to the small size and low cost of the device, emergency vehicles and emergency rooms may maintain a supply of such devices to utilize the potential life-saving effects of the treatment. As a result, many lives can be saved.

Figure 8:
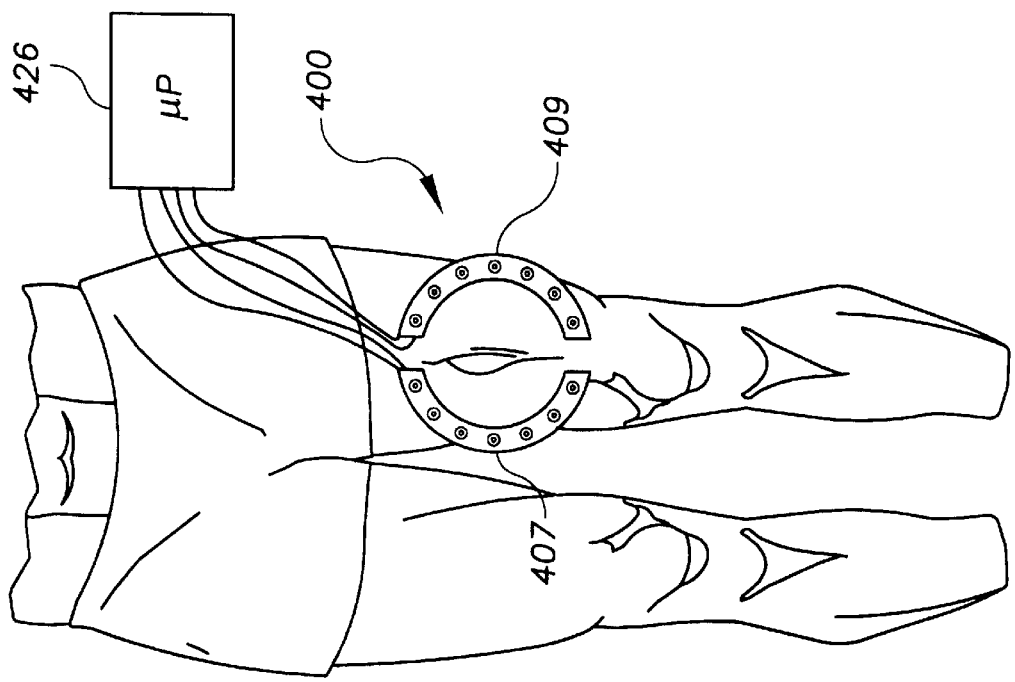
FIG. 8 is a plan view of the laser therapeutic device shown in FIG. 7 as attached to a patient.
Figure 7:
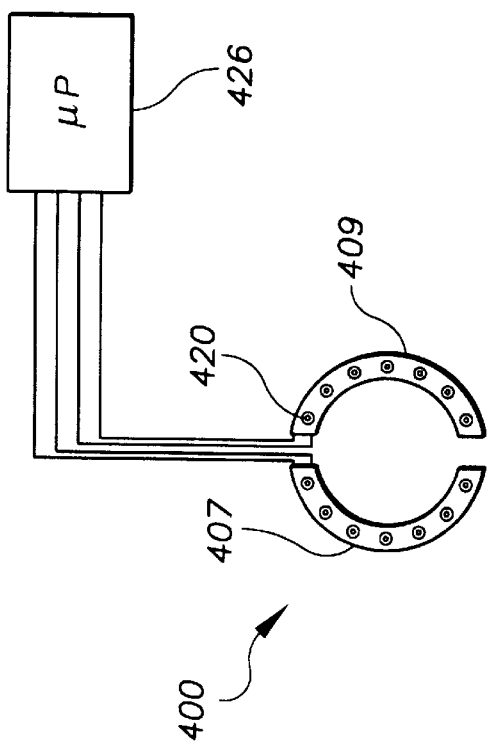
FIG. 7 is a plan view of a third embodiment of a laser therapeutic device in accordance with the present invention.

FIGS. 7–8 illustrates a third embodiment of a laser therapeutic device 400 in accordance with the present invention. The embodiment shown in FIG. 7 is used to surround an area of treatment interest and may also be used to treat ulcers or open wounds located on a patient's body. The device 400 includes two side bandage sections, including a first semicircular or half-moon shaped bandage section 407 and a second semi-circular or half-moon shaped bandage section 409. Each section carries a plurality of VCSEL chips 420 connected in series and are sandwiched between an optically-clear biocompatible polymer allowing transmission of the laser beam. The controller/power supply 426 are mounted on a separate circuit.

The "split bandage" 407, 409 is attached to the patient's skin by medical adhesive to a clear polyurethane wound dressing such as OpSite. The control circuit/power supply module is housed in a biocompatible polymer housing and may be worn on the patient's leg or other convenient location of the body or carried by the patient in a portable fashion. The device may also have an LED mounted an the controller/power supply 426, as discussed above, to indicate this operational status of the device 400 as well as the battery status. As discussed above, the sterile, optically-clear disposable sheet may be a microporous hydrophobic membrane (MHM) material known in the art and used to prevent bacterial contamination of the skin, wound and device. The split bandage would be applied to the MHM using a known medical adhesive.

In operation, as shown in FIG. 8, the device 400 is affixed to the leg of a patient using a medical adhesive. A clear hydrogel wound dressing is first placed over the wound, and a clear polyurethane hydrocellular membrane sheet then placed over the hydrogel. In the case of a venous ulcer, the first layer of a multi-layer compression dressing comprising a gauze layer or a clear, hightly porous contact layer such as Profore non-adherent dressing by Smith-Nephew is placed. The device 400 is then affixed to the periphery of the wound and several layers of compressive dressing placed over the wound and device 40. In the case of a pressure ulcer, Intrasite Gel (Smith-Nephew) may be applied to aid in debriding the wound and then a clear wound dressing such as OpSite Plus Composite dressing placed thereon. Alternatively, in large intracavity pressure ulcers, Allevyn Cavity wound dressing may be placed first, then a clear dressing such as OpSite (Smith-Nephew) next, before affixing the device 400. Alternatively, an MHM sterile clear sheet as discussed above may be placed over the wound and the split bandage sections 407, 409 applied to the sheet using a known medical adhesive.

The spacing between the split bandage sections 407, 409 may be varied to cover a larger or smaller area of the patient's body. The laser energy can then penetrate the patient's skin and "surround" a particular area. As the wound heals, the split bandage sections 407 409 may be moved closer together to maintain their relationship with the edge of the wound. The device may also be used to deliver a treatment to distinct areas of the body using one power supply/controller.

Figure 9:
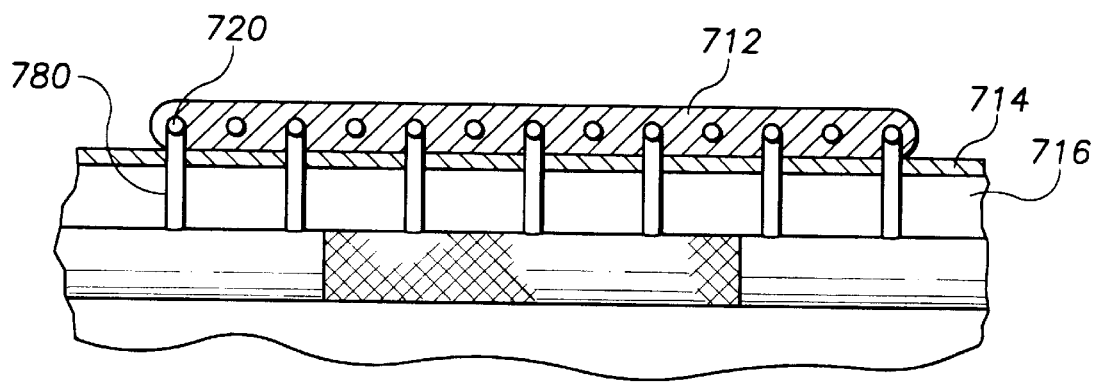
FIG. 9 is a side view of a fourth embodiment of a laser therapeutic device in accordance with the present invention.

FIG. 9 illustrates a fourth embodiment of the laser treatment device of the present invention, that delivers laser beam energy directly to deeper body structures through implanted fiberoptic strands or waveguides. Using interstitial low-level laser therapy (ILLLT) or percutaneous low-level laser therapy (PLLLT), the required energy can reach the desired area at the required depth to produce a biostimulation effect on the targeted area. This embodiment is similar to the second embodiment, the difference being that lasers 720 are coupled to fiberoptic strands or waveguides 780. The fiberoptic strands are coupled to the VCSELs 720 using a plate (not shown) having a thickness of approximately 100 micrometers. The narrow, circular beam characteristic of VCSELs allows for high coupling efficiency to fibers. The plate is affixed to the VCSEL using optically clear epoxy and embedded in a polymer housing 712. The optical fibers 780 may be as small as a typical surgical suture or as in the case of a waveguide, as small as one millimeter or less in diameter.

The fiberoptic strands 780 extend through the patient's dermal layers 714, 716 and related tissues to conduct the laser beam to the targeted area (e.g., pancreas, kidney, heart, vasculature) when the targeted area is beyond the reach of the devices discussed above. The optical fibers may be fitted with various lenses to focus or defocus the beam, including side firing lenses to further direct and guide the laser beam as required. As in the preceding embodiments, a controller/power supply circuit is used to control operation and timing of the lasers 720.

In operation, the optical fibers or waveguides 780 may be implanted along the location of a surgical incision or the optical fibers or waveguides may be percutaneously implanted with an 18 gauge needle implanting device using ultrasound and MRI guidance to the desired location requiring laser therapy. This minimally invasive method of laser therapy delivery may be directed through the skin to the pancreas, kidney, heart or deeper vasculature through the optical fibers 780. In the case of leg ulcers or foot ulcers that have progressed to osteomyelitis (infected bone), the required laser energy would be delivered to the targeted site of the bone infection. Additionally, by increasing the circulation to the targeted area by this device, antibiotic therapy or drug therapy normally prescribed to treat the infection would be able to reach the area of bone infection at a greater level, thus increasing the effectiveness of the drug therapy. The optical fibers can remain in place until the required laser therapy is completed. Once the therapy is completed, the optical fibers 780 may be removed from the patient much like a suture. At that time, a laser bandage device 210 (FIGS. 5–6) may be placed over the surgical area to provide a long-term maintenance dose of laser therapy. As with other embodiments described above, this embodiment is not limited to applications described above but may be applied to vascular grafts, organ transplants, internal vasculature, deep wounds, bones, nerves, and any other body tissue, organ or body cavity.

Figure 10:
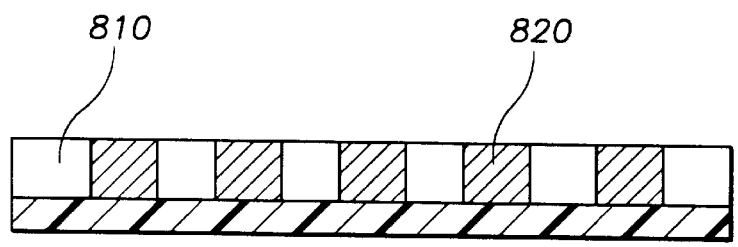
FIG. 10 is a side section view of a fifth embodiment of a laser therapeutic device in accordance with the present invention.
Figure 11:
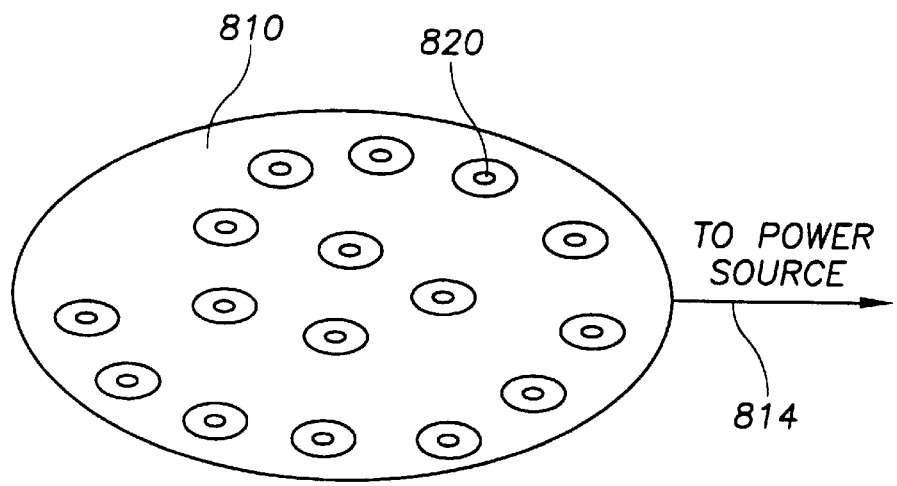
FIG. 11 is a plan view of the laser therapeutic device shown in FIG. 10 having a disc configuration.
Figure 12:
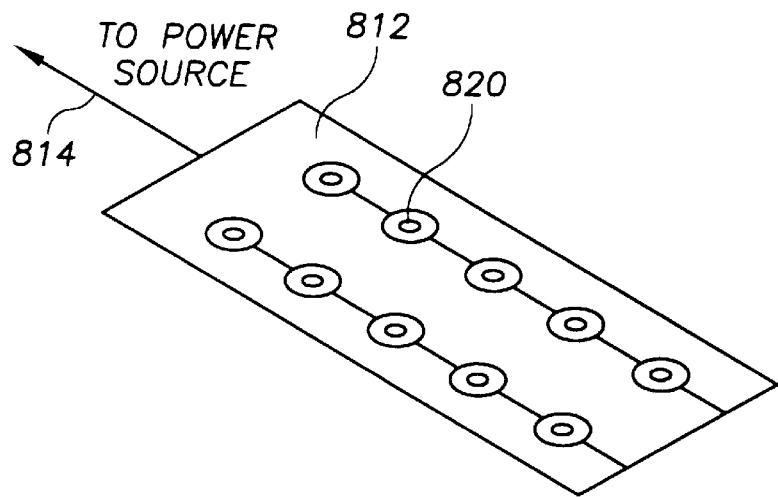
FIG. 12 is a plan view of the laser therapeutic apparatus shown in FIG. 10 having a strip configuration.

FIGS. 10–12 shows a fifth embodiment of the laser treatment device of the present invention. In this embodiment, low level laser energy is delivered to the area of interest through an implantable disc 810 or strip 812 of VCSELs. The disc 810 (see FIG. 11) is formed of a polymer circuit material and has a diameter between 18 and 30 millimeters. The strip 812 (see FIG. 12) has similar construction to that of the disc 810, though it has a rectangular shape. With VCSELs 820 disposed thereon, the disc 810 or strip 812 has a preferred thickness of less than 400 micrometers and is sealed in an optically clear hydrophobic implantable grade biocompatible polymer or a microscopic polymer coating, such as parylene (Cookson Co.).

A number of individual VCSELs or VCSEL arrays 820 are mounted onto the device and are connected in series, such as by electrically conductive printed ink interconnects. The VCSEL arrays 820 are arranged at intervals on the disc 810 or strip 812 to distribute laser energy over an affected area. Preferably, the device includes four VCSEL arrays, with each array containing 2–4 VCSELS. Each VCSEL has an operating power within a range of 2–5 mw. The disc 810 or strip 812 each further include an electrical contact 814 which permits connection to an implantable electrical lead connected to a controller/power supply (as described above). The controller/power supply would be attached to the patient's body and would be positioned in a convenient location on the patient's body proximate to the area of implantation of the disc.

In operation, the controller may be programmed to operate the disc 810 or strip 812 in either a pulsed mode or a continuous wave mode (CW) mode. In the pulsed mode, the VCSEL arrays 820 may operate at a power level of 1 watt for a nanosecond, with the total photon density and average power being less than in the CW mode. In the CW mode, the controller may be programmed to fire each VCSEL array 820 in sequence or all VCSEL arrays simultaneously. In the sequential firing mode, the first VCSEL array would emit laser energy for a period of five seconds, for example. Following this period, a second VCSEL array would emit energy for a period of five seconds, etc.

Figure 13:
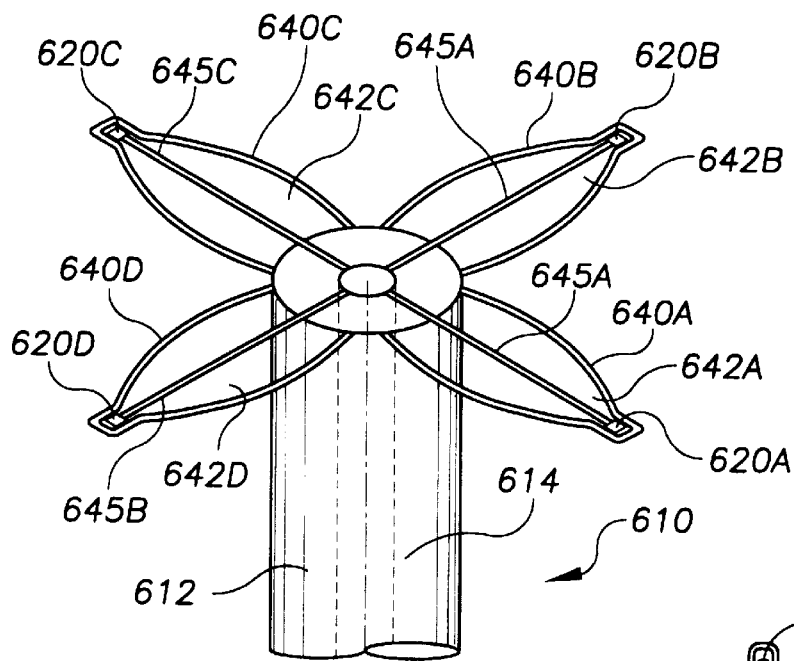
FIG. 13 is a plan view of a sixth embodiment of a laser therapeutic device of the present invention.
Figure 14:
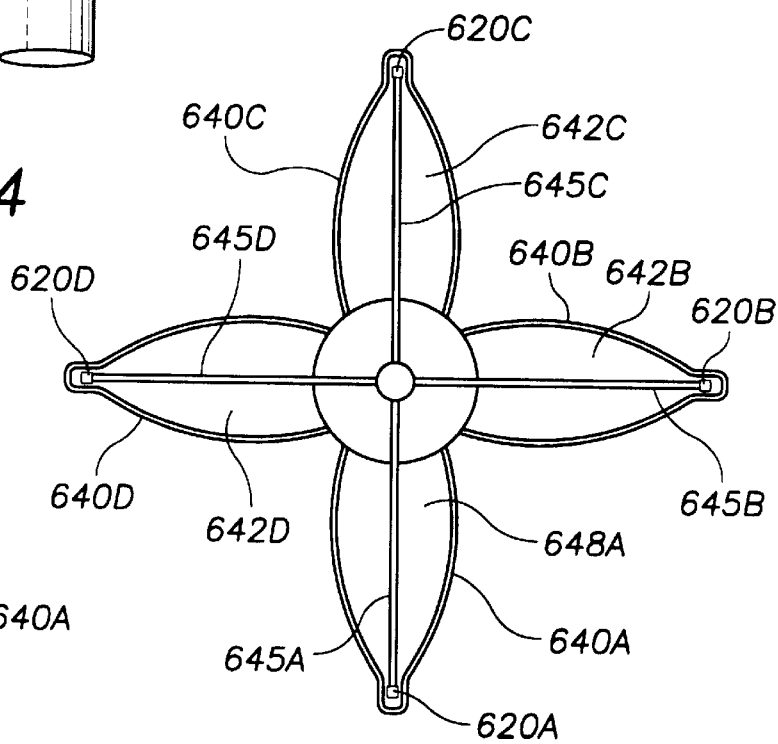
FIG. 14 is a top view of the laser therapeutic device shown in FIG. 13 in a deployed position.
Figure 15:
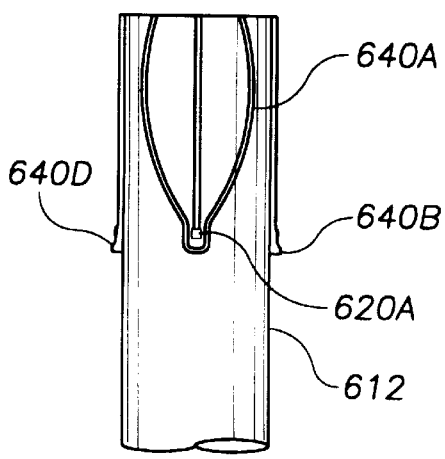
FIG. 15 is a side view of the laser therapeutic device shown in FIG. 13 in a collapsed position.

FIGS. 13–15 show a sixth embodiment of the laser treatment device of the present invention. The implantable device 610 has an "umbrella" shape and features a hollow, cylindrical shaft 612 having an electrical lead 614 coupled to a controller/power supply (not shown). The controller/power supply is similar to the controller/power supply described above with respect to the previous embodiments. A plurality of frames 640A–D are coupled to an end of the shaft 612, with frames overlapping each other proximate the shaft end. Preferably, the frames 640A–D may be comprised of a high strength flexible material, such as superelastic Nitinol. The frames 640A–D surround an electrically non-conductive polymer circuit material 642A–D, respectively, as discussed above. The frames 640A–D gradually extend from the shaft 612 to a wide point before tapering to an outer end.

A VCSEL 620A–D or VCSEL array is mounted on the outer end of each one of the circuits 642A–D, respectively. The VCSELs 620A–D are sealed in clear optical epoxy chip encapsulant. The VCSELs 620A–D are operatively connected by an interconnect 645A–D that runs from each respective VCSEL along the length of each frame 640A–D. Each frame 640A–D is sealed in an optically clear hydrophobic implantable grade biocompatible polymer, or alternatively, a microscopic coating of parylene, to produce a structure that is approximately 300 micrometers in height. Each interconnect 645A–D is connected to the implantable grade electrical lead 614, thus providing power and programmable control to the VCSELs 620A–D.

Optionally, fiberoptic strands may be employed to deliver the laser treatment. In this version, the fiberoptic strands would be carried by the implantable "umbrella" device 610 and the fiberoptic strands after exiting the body would terminate at a coupling plate that is optically coupled to a VCSEL. As discussed above, the optical fibers could be fitted with focusing, defocusing, or side-firing lenses as required.

In operation, when prepared for delivery, each frame 640A–D is initially in an unexpanded position as shown in FIG. 15. In the unexpanded state, the frames 640A–D lie along an outer surface of the shaft 612. The device 610 may be inserted endoscopically by the physician into a treatment area using a trocar or similar guide. Once the device 610 is guided to the targeted area using ultrasound imaging and/or MRI, the physician may deploy the device as shown in FIGS. 13 and 14. Alternatively, the device 610 may be inserted visually and deployed manually by the physician during the course of open surgery and then removed at a later time by minimally invasive surgery or endoscopy. After completing the required laser therapy, the device 610 would be removed by endoscopy and minimally invasive surgery by capturing the frames 640A–D, collapsing the device as shown in FIG. 15, and withdrawing the device through the endoscope. A laser bandage, such as device 210 of FIG. 5, may then be affixed to the skin proximate to the site provide a healing dose of laser therapy to the surgical wound.

Figure 16:
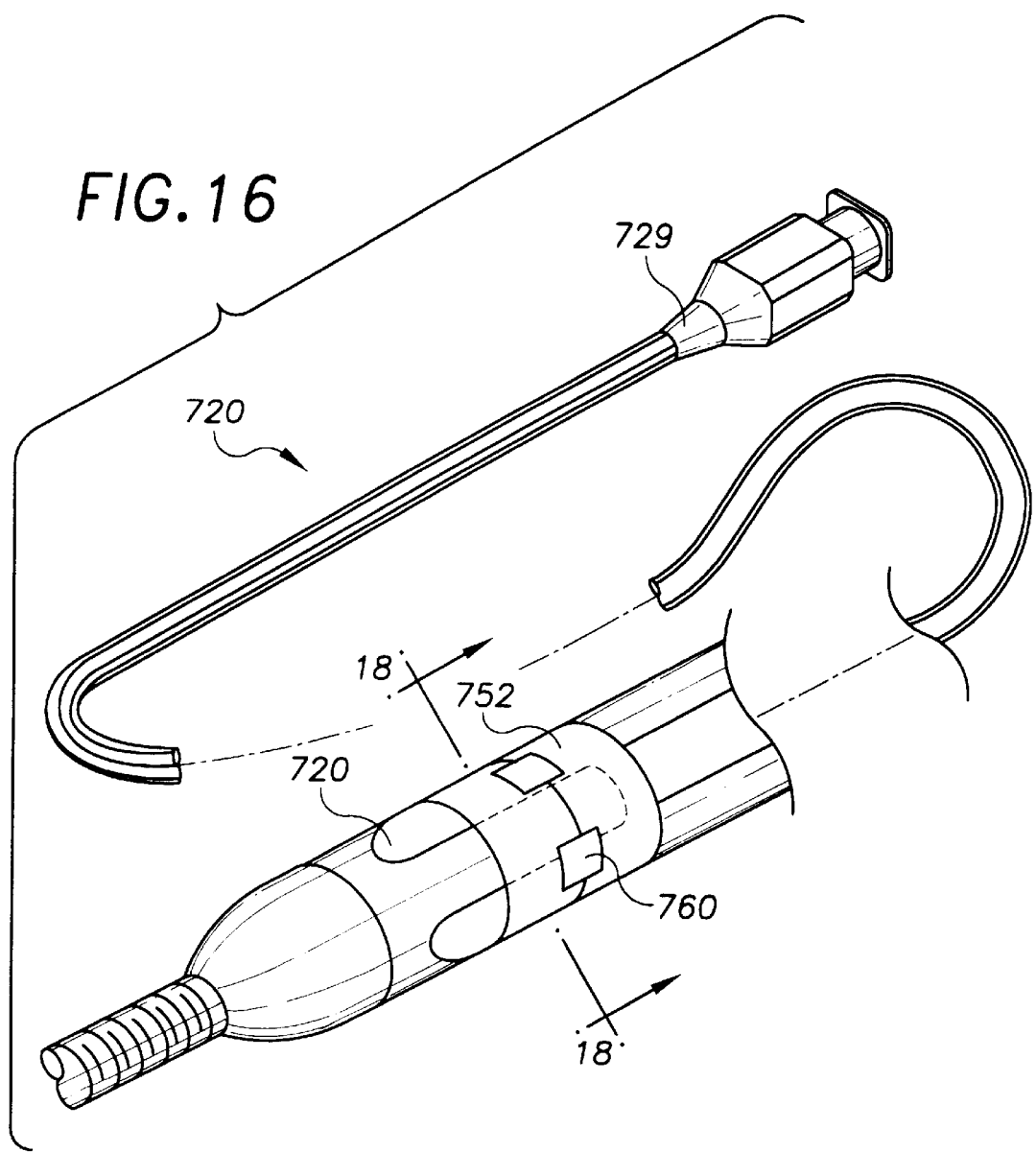
FIG. 16 is a perspective view of a seventh embodiment of the laser therapeutic device of the present invention.
Figure 17:
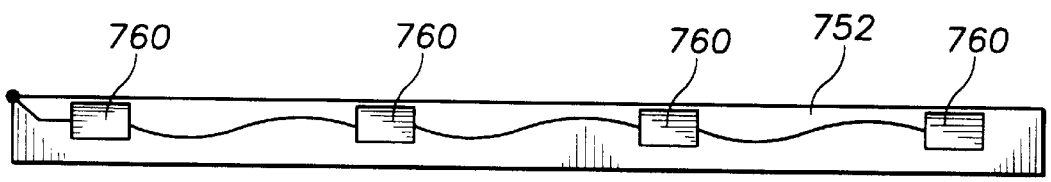
FIG. 17 is an enlarged portion of the laser circuit for use in the laser therapeutic device shown in FIG. 16.
Figure 18:
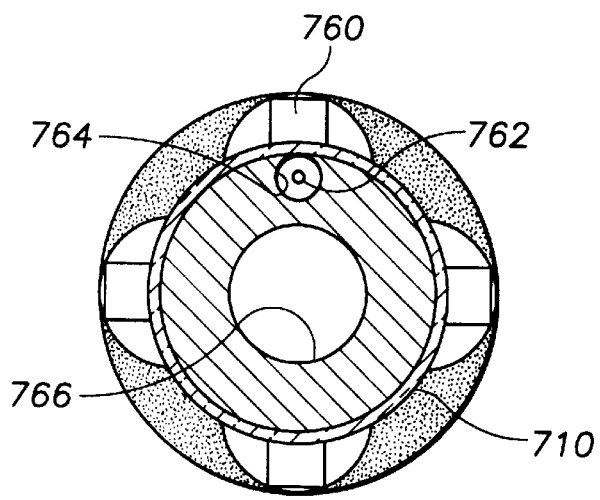
FIG. 18 is an end sectional view of the laser therapeutic device of FIG. 16.

FIGS. 16–18 show a seventh embodiment of the laser treatment apparatus of the present invention. The device 720 includes a non-balloon catheter in which four VCSEL chips 760 are disposed on a circuit material strip 752 and connected in series by printed ink interconnects. The circuit material 752 is positioned circularly around the housing 710 of the catheter and inset into a groove formed in the exterior of the catheter housing so that the profile of the VCSELs is flush with or minimally affects the outer diameter of the catheter. In the embodiment of FIG. 16 there are four VCSELs spaced around the housing 710 at 45° intervals to each other so that when the four VCSELs are powered a laser treatment is delivered in a 180° arc. As in the embodiment of FIG. 3, the VCSELs 760 are provided in an optically clear epoxy encapsulant resulting in a low profile device of approximately 150 microns. In this manner, the circuit material strip 752 with the VCSELs 760 minimally affects the profile of the catheter. An optically clear shrink tubing cover may be applied over the VCSELs 760 to seal and protect the circuit and electrical interconnections. Note that for ease of illustration, the distal end of the catheter 720 is enlarged relative to the proximal end 729 of the catheter.

An electrical lead 762 is connected to the circuit material strip and then enters a separate lumen 764 inside the catheter. The lumen 764 carries the electrical lead 762 to a controller/power supply (not shown) at the proximal end. A guidewire lumen 766 is provided to slide over a guidewire 750, which may be placed in a vessel after a balloon catheter is withdrawn following a balloon angioplasty procedure. Thereafter, the catheter 720 is inserted over the same guidewire to the target area within a vessel or organ. In the case where this embodiment is used in an open surgical procedure or to treat an open deep wound or other body cavity, no guidewire may be necessary.

In operation, when treating large, deep, diabetic ulcers or pressure ulcers, the catheter device 720 is inserted deep into the wound after debridement of necrotic tissue and cleansing of the wound. Thus, the surgeon or the attending medical person may deliver a concentrated dose of laser therapy for 5 to 30 minutes to the entire bed of the ulcer before placing the initial wound dressing. By focusing directly on the targeted area or scanning over the targeted area, laser therapy is provided to irradiate an external or internal surface of an ulcer or wound. After the initial dose is delivered via device 720, the appropriate clear wound dressings would be applied. Thus, in the case of a foot, the laser insole would be placed. For other types of ulcers or for organ stimulation, one of the other embodiments would be selected by the attending medical personnel to deliver ongoing or longer term laser therapy.

Figure 21:
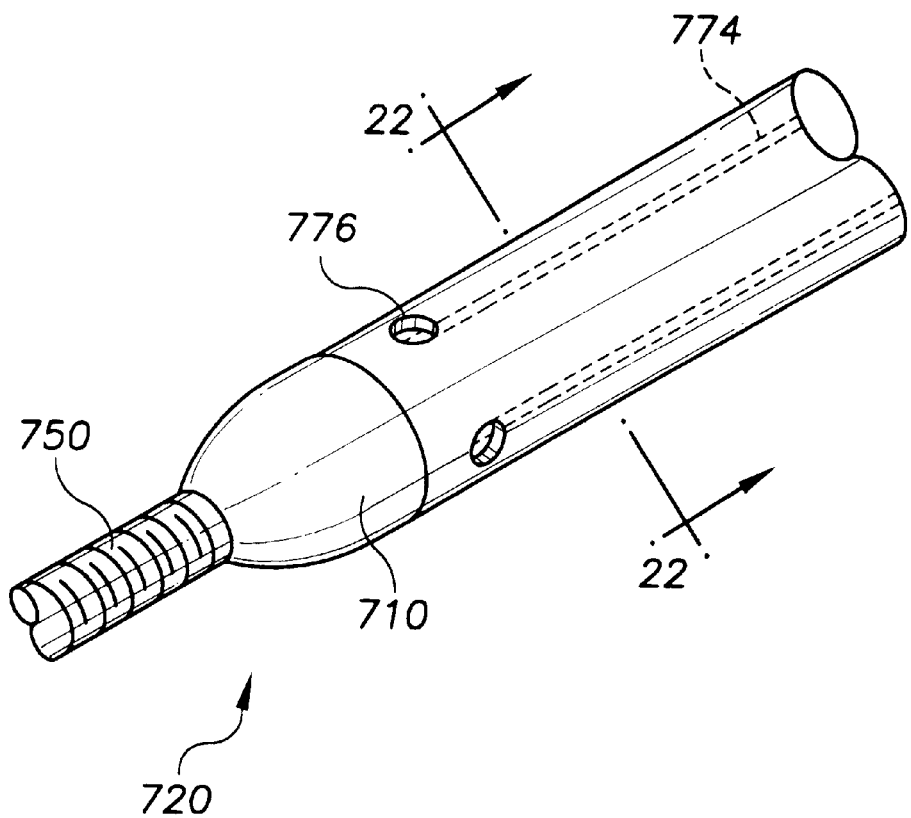
FIG. 21 is a partial perspective view of an alternative construction of the seventh embodiment of the laser therapeutic device of the present invention.
Figure 22:
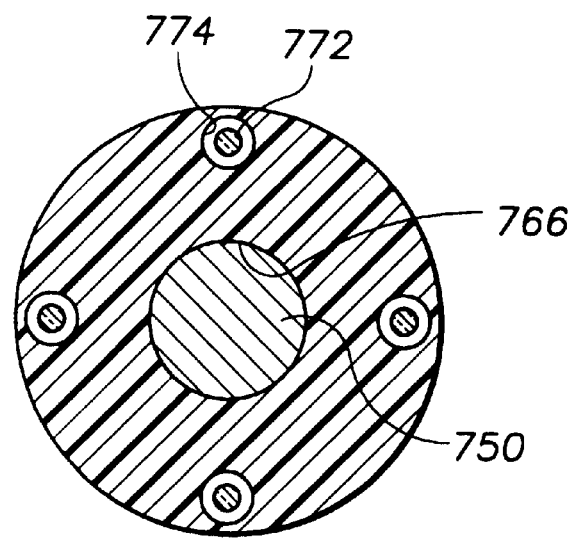
FIG. 22 is an end sectional view of the alternative construction of FIG. 21.

Alternatively, as illustrated in FIGS. 21–22, the device 720 may have a multi-lumen design in which optical fibers 772 extend inside four of the lumens 774. The optical fibers terminate at the surface of the catheter 710 near the distal end at 45° to each other in a circular pattern to provide 180° irradiation to the targeted area. The fibers may be fitted with various lenses 776 (e.g., focusing, defocusing, side firing or ball lens) depending on a desired application. The fibers would couple with VCSELS connected to the power source/controller at the proximal end of the device 720. In this manner, a self-contained laser catheter having an integral power source would provide complete portability.

Figure 23:
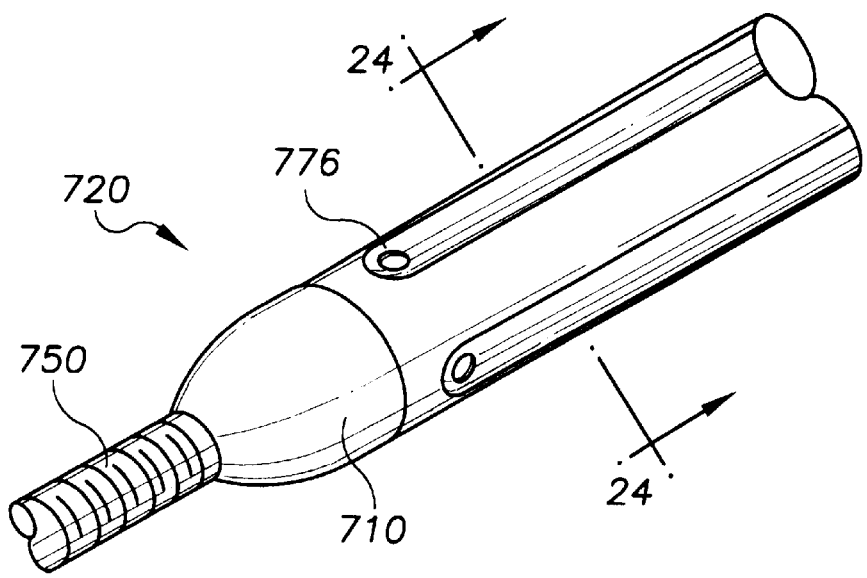
FIG. 23 is a partial perspective view of another alternative construction of the seventh embodiment of the laser therapeutic device of the present invention.
Figure 24:
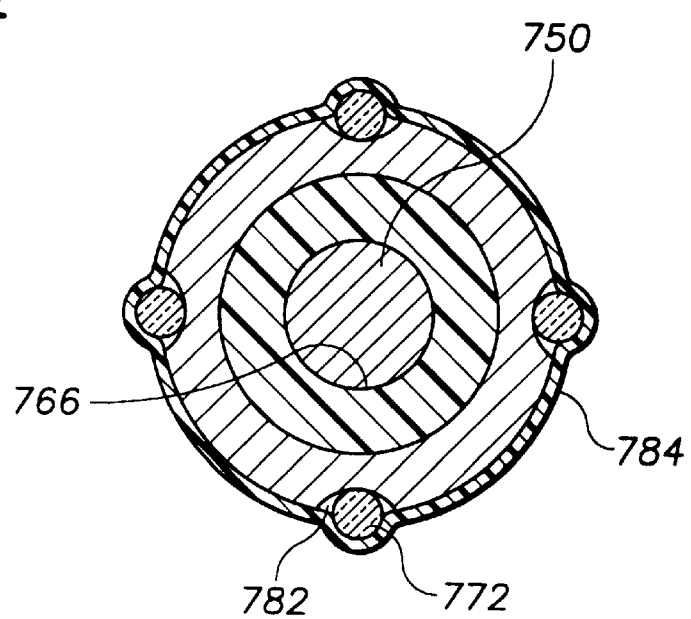
FIG. 24 is an end sectional view of the alternative construction of FIG. 23.

The catheter device 720 may additionally include optical fibers 772 attached to the outside of the body of the catheter housing 710, as illustrated in FIGS. 23–24. The catheter housing 710 may be provided with grooves 782 formed axially along the outer surface, with the optical fibers 772 disposed in the grooves. A shrink tubing cover 784 may be provided over the catheter housing 710 and optical fibers 772. As in FIGS. 21–22, the optical fibers 772 terminate at sides of the housing 710, and may include lenses 776 to permit irradiation in a 180° arc.

Figure 25:
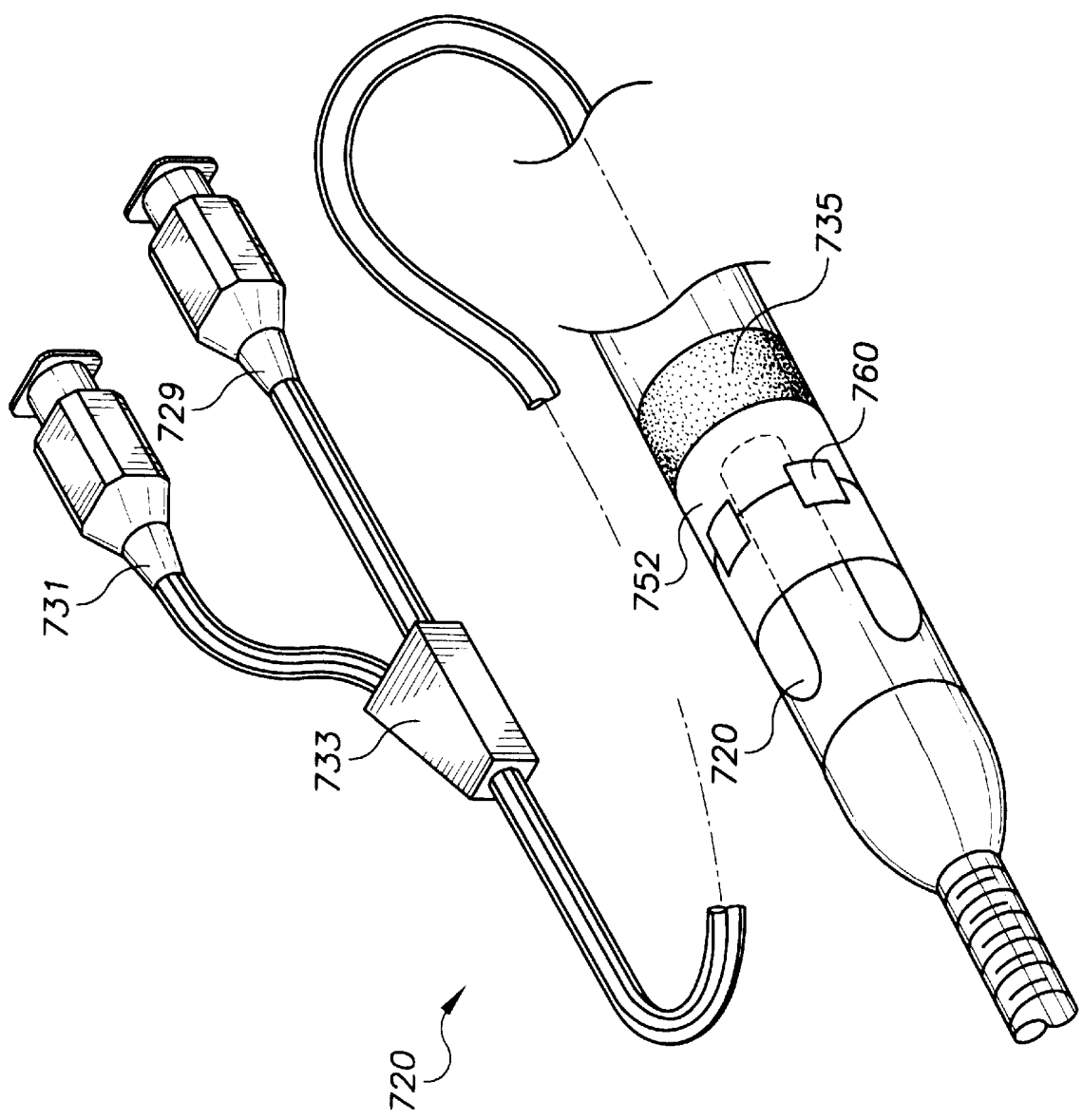
FIG. 25 is a perspective view of another alternative construction of the seventh embodiment of the laser therapeutic device of the present invention.

As illustrated in FIG. 25, the device 720 may also be constructed with a optically clear balloon 735, with the VCSELs adapted to emit laser energy that passes through the balloon. Preferably, the VCSEL circuit would be provided distal to the balloon toward the tip of the catheter. As known in the art, the balloon 735 may be inflated by introduction of a fluid into fluid connection 731 which passes through a lumen in the catheter 720. In operation of the balloon catheter, the VCSELs would deliver an unobstructed laser treatment during balloon inflation and after the balloon is deflated. In larger blood vessels, this embodiment would eliminate the need for an over the wire exchange catheter with VCSELs as this device would be left in place to complete the prescribed treatment regimen. The device 720 may further include the VCSELs positioned directly on the guidewire near the distal end.

Moreover, the device 720 may further comprise optical fibers carried by the guidewire itself and coupled to VCSELs disposed at the proximal end of the device. As noted in the embodiments described above, each optical fiber may be fitted with various lenses to permit irradiation in a 180° arc. In either of these embodiments, the area of interest would continue to receive irradiation after the balloon is withdrawn by leaving the guidewire in place for the prescribed period of time.

Figure 19:
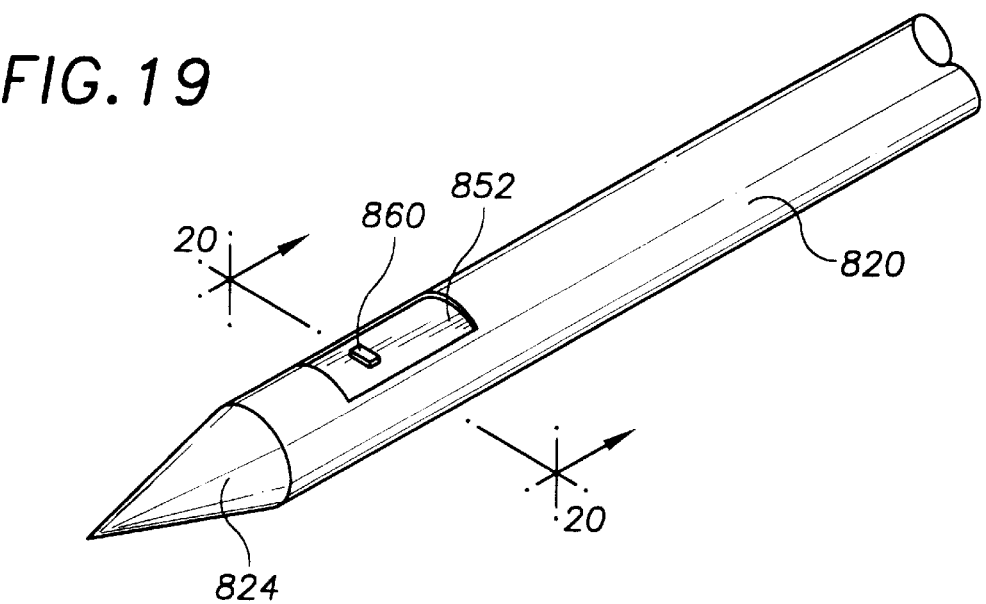
FIG. 19 is a perspective view of an eighth embodiment of the laser therapeutic device of the present invention.
Figure 20:
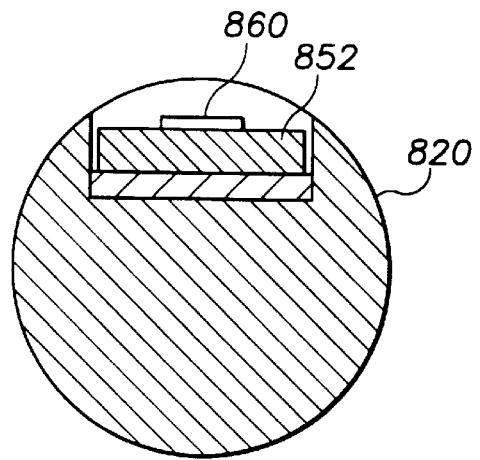
FIG. 20 is an end sectional view of the laser therapeutic device of FIG. 19.

FIGS. 19–20 show yet an eighth embodiment of the present invention in which the VCSELs 860 are disposed on a needle catheter 820 which could be placed inside a blood vessel in the body. The VCSELs 860 are provided on strips 852 of circuit material, in the same manner as the previously described embodiments, with the strips extending along a side surface of the needle catheter 820. Each strip 852 contains one or more chip mounted VCSELs 860 or VCSEL arrays spaced roughly 2 mm apart. Electrical interconnects extending along the length of the strip 852 further permit the surface mounting of various other electronic devices, such as microchip sensors to sense oxygen, carbon dioxide, etc., and/or a digital controller chip to coordinate data flow between the chip sensors and a personal computer.

The needle catheter 820 would enable the operator to insert the laser device in place in a similar manner to an intravenous (IV) catheter. The needle catheter 820 can remain in place for a longer period of time and deliver a larger dose of LLLT to the blood system without interfering with blood flow. As discussed above, various sensors could send important physiological data to the controller/power supply. The controller/supply module could also contain a wireless LAN module which permits high-performance wireless LAN communications to permit the device to be linked to a server or central computer.

Having thus described a preferred embodiment of a laser treatment device, it should be apparent to those skilled in the art that certain advantages of the within system have been achieved. It should also be appreciated that various modifications, adaptations, and alternative embodiments thereof may be made within the scope and spirit of the present invention. For example, VCSELS have been illustrated, but it should be apparent that the inventive concepts described above would be equally applicable using standard laser diodes or defocused surgical lasers, such as carbon dioxide ($CO^2$) lasers at low power densities. The invention is further defined by the following claims.

I claim:

1. A therapeutic device comprising:
    an insole; and
    a circuit coupled to the insole; and
    where the circuit comprises one or more than one laser for emitting one or more than one beam of laser energy.
2. The device of claim 1, where the laser comprises one or more than one VCSEL.
3. The device of claim 1, further comprising a power supply operatively connected to the one or more than one laser.
4. The device of claim 1, further comprising a controller coupled to the circuit.
5. The device of claim 4, where the controller comprises an on/off switch.
6. The device of claim 4, where the controller comprises a pressure switch.
7. The device of claim 4, where the controller is programmable.
8. The device of claim 7, where the controller is programmed to selectively enable the one or more than one laser to emit the beam for a predetermined time at a plurality of predetermined intervals.
9. The device of claim 7, where the laser comprises one or more than one VCSEL; and
    where the controller is programmed to enable the one or more than one VCSEL.
10. The device of claim 7, where the laser comprises one or more than one VCSEL; and
    where the controller is programmed to sequentially enable at least two of the one or more than one VCSEL.
11. The device of claim 7, where the laser comprises one or more than one VCSEL; and
    where the controller is programmed to simultaneously enable at least two of the one or more than one VCSEL.
12. The device of claim 4, further comprising a logic circuit for storing data corresponding to a treatment regimen operatively connected to the controller.
13. The device of claim 4, where the insole comprises a circuit material; and
    where the laser and the controller are disposed on the circuit material.
14. The device of claim 13, where the circuit material comprises an optically clear, biocompatible material.

* * * * *